United States Patent [19]

Son et al.

[11] Patent Number: 5,747,500
[45] Date of Patent: May 5, 1998

[54] ANTIVIRAL 2,4-PYRIMIDINEDIONE DERIVATIVES

[75] Inventors: Jong-Chan Son; Ill-Young Lee, both of Daejeon; Byung-Il Bae, Seoul; Jeong-Sik Han; Joong-Kwon Choi, both of Daejeon; Yung-Bok Chae, Seoul, all of Rep. of Korea

[73] Assignee: Korea Research Institute of Chemical Technology, Daejeon, Rep. of Korea

[21] Appl. No.: 656,354

[22] PCT Filed: Dec. 20, 1994

[86] PCT No.: PCT/KR94/00178

§ 371 Date: Jun. 18, 1996

§ 102(e) Date: Jun. 18, 1996

[87] PCT Pub. No.: WO95/18109

PCT Pub. Date: Jul. 6, 1995

[30] Foreign Application Priority Data

| Dec. 21, 1993 | [KR] | Rep. of Korea | 93-28908 |
| Dec. 21, 1993 | [KR] | Rep. of Korea | 93-28909 |
| May 11, 1994 | [KR] | Rep. of Korea | 94-10262 |
| May 11, 1994 | [KR] | Rep. of Korea | 94-10263 |
| May 11, 1994 | [KR] | Rep. of Korea | 94-10264 |
| Nov. 10, 1994 | [KR] | Rep. of Korea | 94-29388 |

[51] Int. Cl.$^6$ .................. C07D 239/54; C07D 239/56; A61K 31/505
[52] U.S. Cl. .................. 514/274; 514/86; 544/300; 544/301; 544/302; 544/303; 544/304; 544/306; 544/243; 544/309; 544/310; 544/311; 544/312; 544/313; 544/314
[58] Field of Search .................. 514/274, 86; 544/300, 544/301, 302, 303, 304, 309, 312

[56] References Cited

U.S. PATENT DOCUMENTS 5,162,326  11/1992  Naka et al. .................. 544/309

Primary Examiner—John M. Ford
Attorney, Agent, or Firm—Anderson, Kill & Olick, P.C.

[57] ABSTRACT

Novel 2,4-pyrimidinedione compounds, and pharmaceutically acceptable salts thereof which possess good antiviral activities, and specifically represented by the following formula(I):

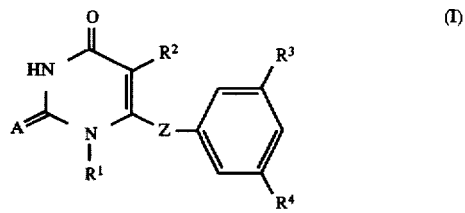

wherein:

$R^1$ represents an unsubstituted or substituted allyl group represented by $CH_2CH=CR^5R^6$ or an unsubstituted or substituted propargyl group represented by $CH_2C\equiv CR^7$ wherein $R^5$, $R^6$ and $R^7$ are each independently a hydrogen atom; a methyl group optionally substituted with a halogen atom, or a $C_{1-10}$ carbonyloxy, hydroxy, azido, cyano, optionally substituted amino, optionally substituted phosphonyl, optionally substituted phenyl, $C_{3-10}$ heteroaryl, $C_{1-3}$ alkoxy or benzyloxy radical; a $C_{2-10}$ alkyl or alkenyl group; a cyclopropyl group; an optionally substituted phenyl group; a $C_{3-10}$ heteroaryl group; a $C_{1-10}$ ester group; or an optionally substituted $C_{1-10}$ alkylamide group;

$R^2$ represents a halogen atom, an optionally substituted $C_{1-5}$ alkyl, $C_{3-6}$ cycloalkyl, $C_{2-8}$ alkenyl, $C_{2-8}$ alkynyl group or a benzyl group;

$R^3$ and $R^4$ represent independently a hydrogen or halogen atom, or a hydroxy, $C_{1-3}$ alkyl, fluoromethyl, $C_{1-3}$ alkoxy, amino, $C_{2-6}$ alkylester or $C_{2-7}$ alkylamide group;

A represents an oxygen or sulfur atom;

Z represents an oxygen or sulfur atom; a carbonyl group; an amino group; or a methylene group optionally substituted with at least one selected from the group consisting of a halogen atom, and a cyano, hydroxy, azido, amino, $C_{1-3}$ alkylamide, $C_{1-4}$ ester, and nitro groups.

5 Claims, No Drawings

ANTIVIRAL 2, 4-PYRIMIDINEDIONE DERIVATIVES

This is a 371 of PCT/KR94/00178 filed Dec. 20, 1994, published as WO95/18109 Jul. 6, 1995.

1. Field of the Invention

The present invention relates to novel pyrimidinedione derivatives, which are useful as an antiviral agent, particularly as a treating agent for acquired immunodeficiency syndrome (AIDS), and pharmaceutically acceptable salts thereof. The invention also relates to processes for the preparation of such derivatives and to pharmaceutical compositions containing same as active ingredients.

2. Description of the Prior Art

Various compounds such as AZT (3'-azido-3'-deoxythymidine); DDC (2',3'-dideoxycytidine), DDI (2',3'-dideoxyinosine) and D4T (3'-deoxy-2',3'-didehydrothymidine) have been reported to have the ability, albeit limited, to inhibit the reproduction of AIDS virus; and they are also known to produce undesirable side effects due to their toxicity.

In order to minimize such problems, therefore, many attempts have been made. For example, 2,4-pyrimidinedione derivatives substituted with an alkoxymethylene group on the N-1 position thereof have been published in J. Med. Chem., 35, 4713 (1992); J. Med. Chem., 35, 337 (1992); J. Med. Chem., 34, 1508 (1991); J. Med. Chem., 34, 1394 (1991); J. Med. Chem., 34, 349 (1991); Molecular Pharm., 39, 805 (1991); Molecular Pharm., 44, 694 (1993); EP 0,449,726 A1; EP 0,420,763 A2; and U.S. Pat. No. 5,318, 972 and reported to have an improved activity against human immunodeficiency virus (HIV), while exhibiting a lower toxicity. However, needs have continued to exist for effective compounds with excellent potency against HIV with a lower toxicity.

The present inventors have studied for a long time in search for 2,4-pyrimidinedione compounds which have a strong activity against HIV as well as a lower toxicity, and, as a result, have discovered that 2,4-pyrimidinedione compounds with an allyl or propargyl group in the N-1 position of the 2,4-pyrimidinedione ring exhibit strong antiviral activities against HIV.

SUMMARY OF THE INVENTION

Accordingly, it is a primary object of the present invention to provide novel compounds having superior antiviral activities against HIV with reduced toxicity.

It is another object of the present invention to provide pharmaceutical compositions containing same.

It is a further object of the present invention to provide processes for the preparation of said novel compounds.

In accordance with one aspect of the present invention, there are provided novel 2,4-pyrimidinedione compounds of formula(I):

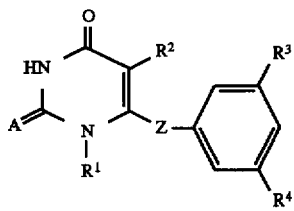

(I)

wherein:

$R^1$ represents an unsubstituted or substituted allyl group represented by $CH_2CH=CR^5R^6$ or an unsubstituted or substituted propargyl group represented by $CH_2C\equiv CR^7$ wherein $R^5$, $R^6$ and $R^7$ are each independently a hydrogen atom; a methyl group optionally substituted with a halogen atom, or a $C_{1-10}$ carbonyloxy, hydroxy, azido, cyano, optionally substituted amino, optionally substituted phosphonyl, optionally substituted phenyl, $C_{3-10}$ heteroaryl, $C_{1-3}$ alkoxy or benzyloxy radical; a $C_{2-10}$ alkyl or alkenyl group; a cyclopropyl group; an optionally substituted phenyl group; a $C_{3-10}$ heteroaryl group; a $C_{1-10}$ ester group; or an optionally substituted $C_{1-10}$ alkylamide group;

$R^2$ represents a halogen atom, an optionally substituted $C_{1-5}$ alkyl, $C_{3-6}$ cycloalkyl, $C_{2-8}$ alkenyl or $C_{2-8}$ alkynyl group, or a benzyl group;

$R^3$ and $R^4$ represent independently a hydrogen or halogen atom, or a hydroxy, $C_{1-3}$ alkyl fluoromethyl, $C_{1-3}$ alkoxy, amino, $C_{2-6}$ alkylester or $C_{2-7}$ alkylamide group;

A represents an oxygen or sulfur atom;

Z represents an oxygen or sulfur atom; a carbonyl group; an amino group; or a methylene group optionally substituted with at least one selected from the group consisting of a halogen, and a cyano, hydroxy, azido, amino, $C_{1-3}$ alkylamide, $C_{1-4}$ ester, and nitro groups.

In accordance with another aspect of the present invention, there are provided pharmaceutically acceptable salts of the compounds of formula(I).

In accordance with a further aspect of the present invention, there are provided pharmaceutical compositions comprising one or more of the 2,4-pyrimidinedione compounds represented by formula(I) and their salts as active ingredients and pharmaceutically acceptable carriers and/or adjuvants.

In accordance with still another aspect of the present invention, there are provided with processes for preparing the 2,4-pyrimidinedione compounds.

DETAILED DESCRIPTION OF THE INVENTION

Among the compounds of the present invention, preferred compounds are those wherein: $R^2$ is an optionally substituted $C_{1-5}$ alkyl group and/or A is an oxygen atom and/or Z is an oxygen or sulfur atom, or a carbonyl or methylene group.

The 2,4-pyrimidinedione compound of formula(I) of the present invention may be prepared by reacting a compound of formula(II) with a compound of formula(III), as shown in Reaction Scheme (1):

Reaction Scheme (1)

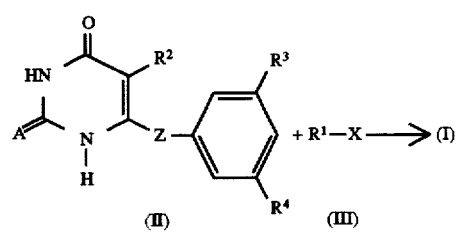

wherein:

A, $R^1$, $R^2$, $R^3$, $R^4$ and Z have the same meanings as defined above;

X represents a halogen atom or a sulfonyloxy group.

The above reaction may be conducted in the presence of a base and a solvent at a reaction temperature ranging from 0° to 100° C. under a nitrogen blanket and in a molar ratio of the compound (II) and the compound (III) ranging from 1:0.8 to 1:1.2. Representative of the base include anhydrous potassium carbonate, anhydrous sodium carbonate, potassium tert-butoxide and the like. The solvent is preferably polar and representative thereof include dimethylformamide, dimethylsulfoxide, hexamethylphosphoramide and the like.

The compounds(II) used as the starting material in the preparation of the 2,4-pyrimidinedione compounds may be prepared by using the methods as shown in Reaction Scheme (2) depending on the Z group.

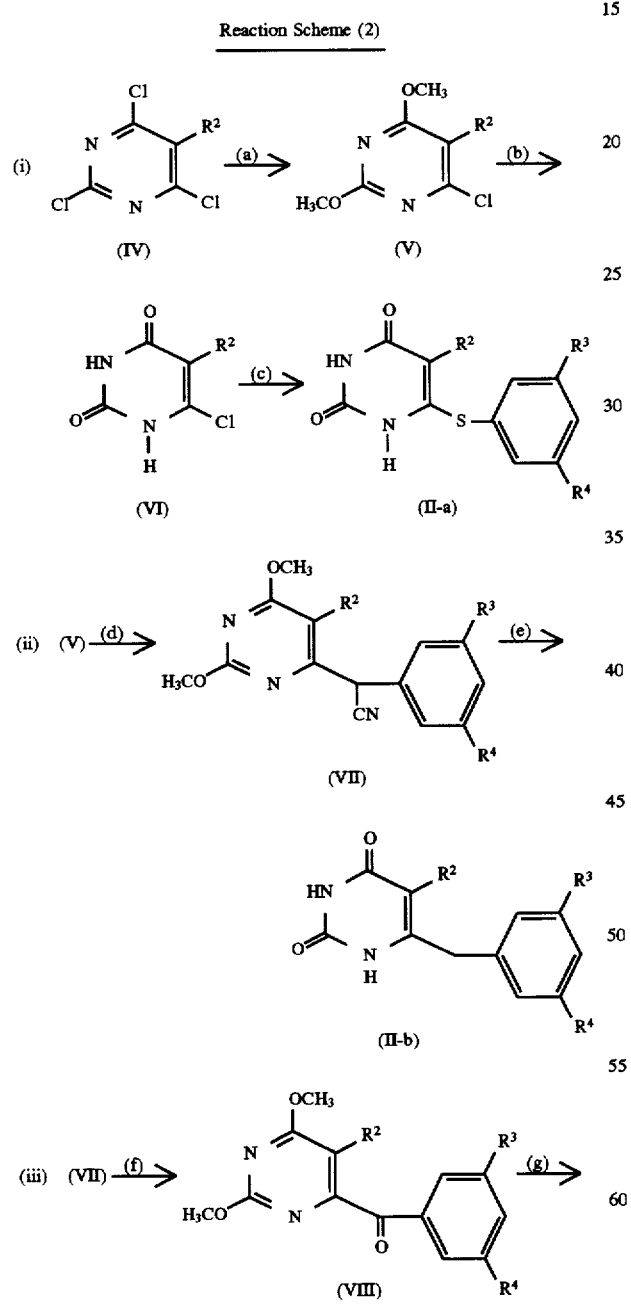

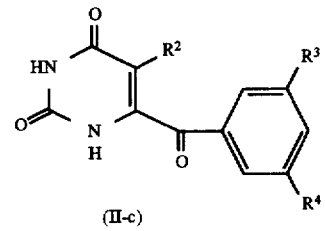

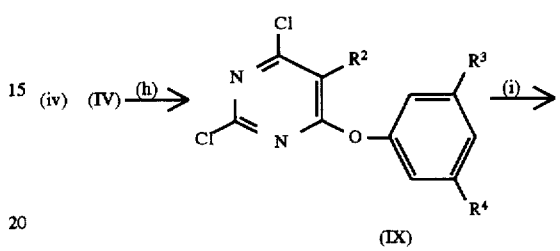

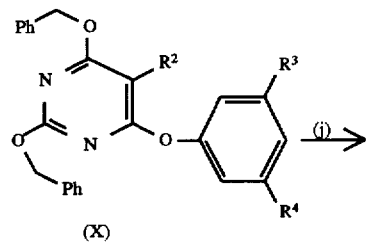

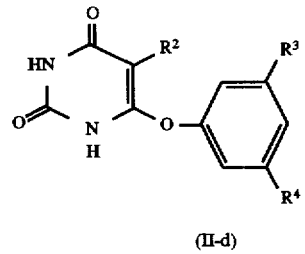

wherein:

$R^2$, $R^3$ and $R^4$ have the same meanings as defined previously.

In accordance with the method (i), a compound of formula (IV) is reacted using a known method disclosed in, e.g., Ber., 52B, 869 (1919) and J. Med. Chem., 7, 808 (1964) to provide a compound of formula (V) (step (a)), which is hydrolyzed with an acid, e.g., hydrochloric acid, to provide a compound of formula (VI) (step (b)). Thereafter, the compound (VI) is reacted with an arylthio compound, e.g., 3,5-dimethylthiophenol, in an alcoholic solvent, e.g., ethanol, in the presence of a base, e.g., potassium hydroxide, to provide a compound of formula (II-a) (step (c)).

In the method (ii), the compound of formula (V) obtained in step (a) above is reacted with an arylacetonitrile compound, e.g., 3,5-dimethylphenylacetonitrile, and a base, e.g., sodium hydride, in a polar solvent, e.g., dimethylformamide, under a nitrogen blanket to provide a compound of formula (VII) (step (d)), which is hydrolyzed by the method described in the step (b) above to provide a compound of formula (II-b) (step (e)).

Further, in accordance with the method (iii), the compound of formula (VII) obtained in step (d) above is reacted with a base, e.g., sodium hydride, in a polar solvent, e.g., dimethylformamide, under an oxygen containing atmosphere to provide a compound of formula (VIII) (step (f)), which is hydrolyzed by the method described in the step (b) above to provide a compound of formula (II-c) (step (g)).

In accordance with the method (iv), the compound of formula (IV) is reacted with phenol in a polar solvent, e.g., dimethylformamide, in the presence of a base, e.g., sodium hydride, to provide a compound of formula (IX) (step (h)), which is reacted with an organometallic compound, e.g., sodium benzylate in an aprotic solvent, e.g., toluene, to provide a compound of formula (X) (step (i)). Thereafter, the compound (X) is subjected to a hydrogen addition reaction in an alcoholic solvent, e.g., ethanol in the presence of a palladium catalyst, e.g., 10% palladium-on-carbon, to provide a compound of formula (II-d) (step (j)).

The compounds of formula (III) used in the present invention are commercially available.

Exemplary compounds of Formula(I) of the present invention which can be prepared in accordance with the inventive method described are listed below:

1-allyl-5-ethyl-6-phenylthio-2,4-pyrimidinedione; 1-(2-butenyl)-5-ethyl-6-phenylthio-2,4-pyrimidinedione; 1-cinnamyl-5-ethyl-6-phenylthio-2,4-pyrimidinedione; 1-(3-methyl-2-butenyl)-5-ethyl-6-phenylthio-2,4-pyrimidinedione; 1-(4-ethoxy-2-butenyl)-5-ethyl-6-phenylthio-2,4-pyrimidinedione; 1-(4-benyloxy-2-butenyl)-5-ethyl-6-phenylthio-2,4-pyrimidinedione; 1-propargyl-5-ethyl-6-phenylthio-2,4-pyrimidinedione;

1-allyl-5-ethyl-6-(3,5-dimethylphenylthio)-2,4-pyrimidinedione; 1-(2-butenyl)-5-ethyl-6-(3,5-dimethylphenylthio)-2,4-pyrimidinedione; 1-cinnamyl-5-ethyl-6-(3,5-dimethylphenylthio)-2,4-pyrimidinedione; 1-(methoxycarbonylallyl)-5-ethyl-6-(3,5-dimethylphenylthio)-2,4-pyrimidinedione; 1-(carboxyallyl)-5-ethyl-6-(3,5-dimethylphenylthio)-2,4-pyrimidinedione; 1-(4-chloro-2-butenyl)-5-ethyl-6-(3,5-dimethylphenylthio)-2,4-pyrimidinedione; 1-propargyl-5-ethyl-6-(3,5-dimethylphenylthio)-2,4-pyrimidinedione; 1-(2-butynyl)-5-ethyl-6-(3,5-dimethylphenylthio)-2,4-pyrimidinedione; 1-(3-phenyl-2-propynyl)-5-ethyl-6-(3,5-dimethylphenylthio)-2,4-pyrimidinedione; 1-(2-pentenyl)-5-ethyl-6-(3,5-dimethylphenylthio)-2,4-pyrimidinedione; 1-(4-hydroxy-2-butenyl)-5-ethyl-6-(3,5-dimethylphenylthio)-2,4-pyrimidinedione;

1-(2-butenyl)-5-isopropyl-6-(3,5-dimethylphenylthio)-2,4-pyrimidinedione; 1-(2-pentenyl)-5-isopropyl-6-(3,5-dimethylphenylthio)-2,4-pyrimidinedione; 1-cinnamyl-5-isopropyl-6-(3,5-dimethylphenylthio)-2,4-pyrimidinedione; 1-(methoxycarbonylallyl)-5-isopropyl-6-(3,5-dimethylphenylthio)-2,4-pyrimidinedione; 1-(2-butynyl)-5-isopropyl-6-(3,5-dimethylphenylthio)-2,4-pyrimidinedione; 1-(3-phenyl-2-propynyl)-5-isopropyl-6-(3,5-dimethylphenylthio)-2,4-pyrimidinedione;

1-allyl-5-ethyl-6-benzyl-2,4-pyrimidinedione; 1-(2-butenyl)-5-ethyl-6-benzyl-2,4-pyrimidinedione; 1-cinnamyl-5-ethyl-6-benzyl-2,4-pyrimidinedione;

1-allyl-5-ethyl-6-(3,5-dimethylbenzyl)-2,4-pyrimidinedione; 1-(2-butenyl)-5-ethyl-6-(3,5-dimethylbenzyl)-2,4-pyrimidinedione; 1-cinnamyl-5-ethyl-6-(3,5-dimethylbenzyl)-2,4-pyrimidinedione; 1-(3-methyl-2-butenyl)-5-ethyl-6-(3,5-dimethylbenzyl)-2,4-pyrimidinedione; 1-(methoxycarbonylallyl)-5-ethyl-6-(3,5-dimethylbenzyl)-2,4-pyrimidinedione; 1-propargyl-5-ethyl-6-(3,5-dimethylbenzyl)-2,4-pyrimidinedione; 1-(2-butynyl)-5-ethyl-6-(3,5-dimethylbenzyl)-2,4-pyrimidinedione; 1-(3-phenyl-2-propynyl)-5-ethyl-6-(3,5-dimethylbenzyl)-2,4-pyrimidinedione;

1-(2-butenyl)-5-isopropyl-6-(3,5-dimethylbenzyl)-2,4-pyrimidinedione; 1-cinnamyl-5-isopropyl-6-(3,5-dimethylbenzyl)-2,4-pyrimidinedione; 1-(3-phenyl-2-propynyl)-5-isopropyl-6-(3,5-dimethylbenzyl)-2,4-pyrimidinedione;

1-allyl-5-ethyl-6-(3,5-dimethylbenzoyl)-2,4-pyrimidinedione; 1-(2-butenyl)-5-ethyl-6-(3,5-dimethylbenzoyl)-2,4-pyrimidinedione; 1-(trans-cinnamyl)-5-ethyl-6-(3,5-dimethylbenzoyl)-2,4-pyrimidinedione; 1-(cis-cinnamyl)-5-ethyl-6-(3,5-dimethylbenzoyl)-2,4-pyrimidinedione; 1-(2-pentenyl)-5-ethyl-6-(3,5-dimethylbenzoyl)-2,4-pyrimidinedione; 1-(3-methyl-2-butenyl)-5-ethyl-6-(3,5-dimethylbenzoyl)-2,4-pyrimidinedione; 1-(methoxycarbonylallyl)-5-ethyl-6-(3,5-dimethylbenzoyl)-2,4-pyrimidinedione; 1-(ethoxycarbonylallyl)-5-ethyl-6-(3,5-dimethylbenzoyl)-2,4-pyrimidinedione; 1-(isopropoxycarbonylallyl)-5-ethyl-6-(3,5-dimethylbenzoyl)-2,4-pyrimidinedione; 1-(4-chloro-2-butenyl)-5-ethyl-6-(3,5-dimethylbenzoyl)-2,4-pyrimidinedione; 1-(4-azido-2-butenyl)-5-ethyl-6-(3,5-dimethylbenzoyl)-2,4-pyrimidinedione; 1-(4-acetoxy-2-butenyl)-5-ethyl-6-(3,5-dimethylbenzoyl)-2,4-pyrimidinedione; 1-(4-hydroxy-2-butenyl)-5-ethyl-6-(3,5-dimethylbenzoyl)-2,4-pyrimidinedione; 1-(4-methoxy-2-butenyl)-5-ethyl-6-(3,5-dimethylbenzoyl)-2,4-pyrimidinedione; 1-propargyl-5-ethyl-6-(3,5-dimethylbenzoyl)-2,4-pyrimidinedione; 1-(2-butynyl)-5-ethyl-6-(3,5-dimethylbenzoyl)-2,4-pyrimidinedione; 1-(3-phenyl-2-propynyl)-5-ethyl-6-(3,5-dimethylbenzoyl)-2,4-pyrimidinedione; 1-(2-butenyl)-5-isopropyl-6-(3,5-dimethylbenzoyl)-2,4-pyrimidinedione; 1-cinnamyl-5-isopropyl-6-(3,5-dimethylbenzoyl)-2,4-pyrimidinedione; 1-(2-pentenyl)-5-isopropyl-6-(3,5-dimethylbenzoyl)-2,4-pyrimidinedione; 1-(methoxycarbonylallyl)-5-isopropyl-6-(3,5-dimethylbenzoyl)-2,4-pyrimidinedione; 1-(4-chloro-2-butenyl)-5-isopropyl-6-(3,5-dimethylbenzoyl)-2,4-pyrimidinedione; 1-(4-azido-2-butenyl)-5-isopropyl-6-(3,5-dimethylbenzoyl)-2,4-pyrimidinedione;

1-(4-acetoxy-2-butenyl)-5-isopropyl-6-(3,5-dimethylbenzoyl)-2,4-pyrimidinedione; 1-(4-hydroxy-2-butenyl)-5-isopropyl-6-(3,5-dimethylbenzoyl)-2,4-pyrimidinedione; 1-(2-butynyl)-5-isopropyl-6-(3,5-dimethylbenzoyl)-2,4-pyrimidinedione; 1-(3-phenyl-2-propynyl)-5-isopropyl-6-(3,5-dimethylbenzoyl)-2,4-pyrimidinedione;

1-allyl-5-ethyl-6-(3,5-dimethylphenoxy)-2,4-pyrimidinedione; 1-(2-butenyl)-5-ethyl-6-(3,5-dimethylphenoxy)-2,4-pyrimidinedione; 1-(trans-cinnamyl)-5-ethyl-6-(3,5-dimethylphenoxy)-2,4-pyrimidinedione; 1-(cis-cinnamyl)-5-ethyl-6-(3,5-dimethylphenoxy)-2,4-pyrimidinedione; 1-(4-hydroxy-2-butenyl)-5-ethyl-6-(3,5-dimethylphenoxy)-2,4-pyrimidinedione; 1-propargyl-5-ethyl-6-(3,5-dimethylphenoxy)-2,4-pyrimidinedione; 1-(3-phenyl-2-propynyl)-5-ethyl-6-(3,5-dimethylphenoxy)-2,4-pyrimidinedione; 1-(2-pentenyl)-5-ethyl-6-(3,5-dimethylphenoxy)-2,4-pyrimidinedione; 1-(methoxycarbonylallyl)-5-ethyl-6-(3,5-dimethylphenoxy)-2,4-pyrimidinedione;

1-(2-butenyl)-5-isopropyl-6-(3,5-dimethylphenoxy)-2,4-pyrimidinedione; 1-cinnamyl-5-isopropyl-6-(3,5-dimethylphenoxy)-2,4-pyrimidinedione; 1-(methoxycarbonylallyl)-5-isopropyl-6-(3,5-dimethylphenoxy)-2,4-pyrimidinedione; 1-(2-butynyl)-5-isopropyl-6-(3,5-dimethylphenoxy)-2,4-pyrimidinedione; and 1-(3-phenyl-2-propynyl)-5-isopropyl-6-(3,5-dimethylphenoxy)-2,4-pyrimidinedione.

Furthermore, the present invention encompasses, within its scope, those pharmaceutically acceptable salts of the compounds of formula(I). Suitable pharmaceutically acceptable salts of the 2,4-pyrimidinedione compounds(I) may include alkali or alkaline earth metallic salts, e.g., a sodium, potassium, magnesium, calcium salts and the like. Further, in case that any one of $R^1$, $R^3$ and $R^4$ in formula (I) is an amino group, such inorganic acid salts as a hydrochloride, hydrobromide, sulfate, phosphate, nitrate, perchlorate and the like; and such organic carboxylic and sulfonic acid salts as a formate, acetate, propionate, succinate, glycolate, lactate, fumarate, 4-hydroxybenzoate, methanesulfonate, ethanesulfonate and the like are also included within the scope of the pharmaceutically acceptable salts of the present invention.

As described previously, the 2,4-pyrimidinedione compounds(I) of the present invention and their pharmaceutically acceptable salts possess a strong antiviral activity, particularly against HIV.

The present invention also includes within its scope pharmaceutical compositions comprising one or more of the compounds(I) and their above-mentioned salts as active ingredients, in association with pharmaceutically acceptable carriers, excipients or other additives, if necessary.

The pharmaceutical compositions of the invention may be formulated for administration orally or by injection. The composition for oral administration may take various forms such as tablets and gelatin capsules, which may contain conventional additives such as a diluent (e.g., lactose, dextrose, sucrose, mannitol, sorbitol, cellulose and/or glycine), a lubricant (e.g., silica, talc, stearic acid or its magnesium and calcium salts and polyethylene glycol). In the case of the tablet form, the composition may further comprise a coupling agent (e.g., magnesium aluminum silicate, starch paste, gelatin, tragakans, methyl cellulose, sodium carboxymethyl cellulose and polyvinyl picolidine) and optionally a dusting agent (e.g., starch, agar and alginic acid or its sodium salt), absorbent, colorant, favour, sweetener and the like. The composition for injection may be an isotonic solution or a suspension.

The composition may be sterilized and/or contain an adjuvant such as a preservative, stabilizer, wetting agent, emulsifier, a salt for controlling an osmotic pressure and/or a buffer solution, and other pharmaceutically effective materials.

The pharmaceutical compositions can be prepared by a conventional mixing, granulating or coating method and may comprise preferably about 0.1 to 75%, more preferably about 1 to 50% of an active ingredient. The unit dosage of the composition suitable for the, administration to human of a weight of about 50 to 70 kg may comprise about 10 to 200 mg of the active ingredient.

The following Examples are given for the purpose of illustration only and are not intended to limit the scope of the invention.

In the Examples, unless otherwise specified, the evaporation was conducted under a reduced pressure, preferably under a pressure ranging from about 15 to 100 mmHg, and the flash chromatography was carried out by using Merck Kieselgel 60, 230–400 mesh marketed by Merck.

Preparation 1

Synthesis of 5-ethyl-6-phenylthio-2,4-pyrimidinedione

Step 1) Synthesis of 5-ethyl-6-chloro-2,4-pyrimidinedione

A solution of 32 g (0.16 mol) of 2,4-dimethoxy-5-ethyl-6-chloro-1,3-pyrimidine in 130 ml of conc. HCl was refluxed with stirring. After 4 hours, the reaction mixture was cooled to room temperature to give a light yellow precipitate, which was collected by filtration and recrystallized from dichloromethane-methanol(1:1) to afford 18.4 g (yield 67%) of the title compound as a white solid.

M.p.: 218° to 219° C. $^1$H-NMR(300 MHz, $CD_3OD$) δ 1.06(3H, t, J=7.5 Hz), 2.45(2H, q, J=7.5 Hz) IR(KBr) 3377(w, N—H), 1730 and 1630 $cm^{-1}$(s, CO) m/z(EI) 174 ($M^+$, 100%), 159(M—$CH_3^+$, 94%)

Step 2) Synthesis of 5-ethyl-6-phenylthio-2,4-pyrimidinedione

To a stirred solution of 3.28 g (58.4 mmol) of potassium hydroxide in 120 ml of anhydrous ethanol were added 10.2 g (58.4 mmol) of the compound obtained from step 1 and 7.2 ml (58.4 mmol) of benzenethiol. The resulting mixture was refluxed for 24 hours and evaporated under reduced pressure to give a white precipitate, which was washed with distilled water and recrystallized from ethanol to afford 18.2 g (yield 84%) of the title compound as a white solid.

M.p.: 221° to 223° C. $^1$H-NMR(300 MHz, $CD_3OD$) δ 1.11(3H, t, J=7.5 Hz), 2.58(2H, q, J=7.5 Hz), 7.49(5H, m) IR(KBr) 3379(w, N—H), 1703 and 1632 $cm^{-1}$(s, CO) m/z(EI) 248($M^+$, 63%), 233(M—$CH_3^+$, 100%)

Preparation 2

Synthesis of 5-ethyl-6-(3,5-dimethylphenylthio)-2,4-pyrimidinedione

To a stirred solution of 2.02 g (36 mmol) of potassium hydroxide dissolved in 100 ml of anhydrous ethanol were added 6.28 g (36 mmol) of the compound obtained from step 1 of Preparation 1 and 5 g (36 mmol) of 3,5-dimethylthiophenol. The resulting mixture was refluxed for 24 hours and evaporated under reduced pressure to give a white precipitate, which was washed with distilled water and recrystallized from ethanol to afford 7.5 g (yield 75%) of the title compound as a white solid.

M.p.: 224° to 225° C. $^1$H-NMR(200 MHz, $CD_3OD$) δ 1.14(3H, t, J=7.5 Hz), 2.36(6H, s), 2.55 (2H, q, J=7.5 Hz), 7.06(1H, s), 7.16–7.26(3H, m), 9.04(1H, s) m/z(EI) 276($M^+$, 73%), 261(M—$CH_3^+$, 100%)

Preparation 3

Synthesis of 5-isopropyl-6-(3,5-dimethylphenylthio-2,4-pyrimidinedione

Step 1) Synthesis of 2,4-dimethoxy-5-isopropyl-6-chloro-1,3-pyrimidine

To 50 ml of anhydrous methanol was added 0.46 g (20 mmol) of sodium to produce sodium methoxide, and then 4.51 g (20 mmol) of 2,4,6-trichloro-5-isopropyl-1,3-pyrimidine was added thereto. The resulting mixture was stirred at room temperature for about 24 hours and evaporated under reduced pressure to give an oily residue, which was purified by flash chromatography using a mixture of ethyl acetate and hexane (1:10) as an eluent to afford 4.11 g (yield 95%) of the title compound as a colorless oil.

$^1$H-NMR(200 MHz, CDCl$_3$) δ 1.23(6H, d, J=7.1 Hz), 3.40(1H, m), 3.94(3H, s), 3.97(3H, s)

Step 2) Synthesis of 5-isopropyl-6-chloro-2,4-pyrimidinedione

A solution of 1.00 g (4.619 mmol) of the compound obtained from step 1 in 20 ml of conc. HCl-methanol (1:3) was refluxed with stirring. After about 4 hours, the reaction mixture was evaporated under reduced pressure to give a white solid, which was further purified by recrystallization from chloroform-methanol to afford 581 mg (yield 67%) of the title compound as a white solid.

M.p.: 250° to 251° C. $^1$H-NMR(200 MHz, CDCl$_3$) δ 1.25(6H, d, J=7.1 Hz), 3.13(1H, m) m/z(EI), 188(M$^+$, 39%), 173(M—CH$_3^+$, 100%)

Step 3) Synthesis of 5-isopropyl-6-(3,5-dimethylphenyl-thio)-2,4-pyrimidinedione To a stirred solution of 2 g (10.6 mmol) of the compound obtained from step 2 in 25 ml of ethanol were added 2.2 g (15.9 mmol) of 3,5-dimethylthiophenol and 654 mg (11.7 mmol) of potassium hydroxide. The resulting mixture was refluxed with stirring for 23 hours and evaporated under reduced pressure to give a white solid, which was washed with distilled water and dried under reduced pressure to afford 2.9 g (yield 94%) of the title compound as a white solid.

M.p.: 225° to 226° C. $^1$H-NMR(200 MHz, CDCl$_3$) δ 1.34(6H, d, J=7.1 Hz), 2.35(6H, s), 3.11(1H, m), 7.14(1H, s), 7.16(2H,s), 9.30(1H,s)

Preparation 4

Synthesis of 5-ethyl-6-benzyl-2,4-pyrimidinedione

Step 1) Synthesis of 2,4-dimethoxy-5-ethyl-6-(α-cyanobenzyl)-1,3-pyrimidine

A solution of 20.25 g (0.1 mol) of 2,4-dimethoxy-5-ethyl-6-chloro-1,3-pyrimidine and 14 g (0.12 mol) of phenylacetonitrile in 60 ml of dimethylformamide (DMF) was cooled to 0° C. under an atmosphere of nitrogen and 4.4 g (0.11 mol) of 60% sodium hydride was added with stirring thereto. The resulting mixture was then stirred at room temperature for 16 hours, neutralized with a dil. HCl, extracted with ether, washed with water, dried over anhydrous magnesium sulfate, and evaporated under reduced pressure to give an ivory oily residue. The residue was purified by flash chromatography using a mixture of ethyl acetate and hexane (1:1) as an eluent to afford 17.95 g (yield 63%) of the title compound as a white solid.

M.p.: 73° to 74° C. $^1$H-NMR(200 MHz, CDCl$_3$) δ 0.95 (3H, t, J=7.5 Hz), 2.47–2.59(2H, m), 3.97(3H, s), 4.00(3H, s), 5.31(1H, s), 7.26–7.47(5H, m)

Step 2) Synthesis of 5-ethyl-6-benzyl-2,4-pyrimidinedione

A solution of 3.95 g (14.0 mmol) of the compound obtained from step 1 in 100 ml of conc. HCl was refluxed with stirring. After about 45 hours, the reaction mixture was cooled to room temperature to give a white precipitate, which was collected by filtration and recrystallized from methanol to afford 2.64 g (yield 82%) of the title compound as a white solid.

M.p.: 240° to 241° C. $^1$H-NMR(200 MHz, CDCl$_3$) δ 1.02(3H, t, J=7.5 Hz), 2.74(2H, q, J=7.5 Hz), 4.15(2H, s), 7.18–7.32(5H, m) m/z(EI) 230(M$^+$, 100%), 215(M—CH$_3^+$, 38%)

Preparation 5

Synthesis of 5-ethyl-6-(3,5-dimethylbenzyl)-2,4-pyrimidinedione

Step 1) Synthesis of 2,4-dimethoxy-5-ethyl-6-(α-cyano-3,5-dimethylbenzyl)-1,3-pyrimidine A solution of 13.26 g (65.5 mmol) of 2,4-dimethoxy-5-ethyl-6-chloro-1,3-pyrimidine and 11.4 g (78.6 mmol) of 3,5-dimethylphenylacetonitrile in 120 ml of DMF was cooled to 0° C. under nitrogen and 3.14 g (78.6 mmol) of 60% sodium hydride was added portionwise, with stirring, thereto. The resulting mixture was stirred for 14 hours at room temperature, neutralized with acetic acid, and evaporated under reduced pressure to give a brown-colored residue, which was purified by flash chromatography using a mixture of ethyl acetate and hexane (1:10) as an eluent to afford 13.2 g (yield 65%) of the title compound as a white solid.

M.p.: 86° to 88° C. $^1$H-NMR(200 MHz, CDCl$_3$) δ 0.96 (3H, t, J=7.4 Hz), 2.87(6H, s), 2.46–2.58(2H, m), 3.97(3H, s), 4.01(3H, s), 5.22(1H, s), 6.94(1H, s), 7.02(2H, s)

Step 2) Synthesis of 5-ethyl-6-(3,5-dimethylbenzyl)-2,4-pyrimidinedione

A solution of 2 g (6.43 mmol) of the compound obtained from step 1 in 20 ml of conc. HCl was refluxed with stirring in an oil bath. After 72 hours, the reaction mixture was cooled to room temperature and evaporated under reduced pressure to give a light yellow residue, which was recrystallized from chloroform-methanol to afford 1.28 g (yield 77%) of the title compound as a white solid.

M.p.: 228° to 229° C. $^1$H-NMR(200 MHz, CDCl$_3$) δ 1.02(3H, t, J=7.4 Hz), 2.27(6H, s), 2.42(2H, q, J=7.4 Hz), 3.74(2H, s), 6.79(2H, s), 6.95(1H, s), 7.72(1H, s), 8.50(1H, s)

Preparation 6

Synthesis of 5-ethyl-6-(3,5-dimethylbenzoyl)-2,4-pyrimidinedione

Step 1) Synthesis of 2,4-dimethoxy-5-ethyl-6-(3,5-dimethylbenzoyl)-1,3-pyrimidine To a stirred solution of 2.35 g (7.56 mmol) of the compound obtained from step 1 of Preparation 5 in 50 ml of DMF was added 363 mg (9.07 mmol) of 60% sodium hydride at room temperature under an atmosphere of nitrogen. The resulting mixture was stirred for 4 hours under an air atmosphere, neutralized with acetic acid, and evaporated under reduced pressure to give a light yellow residue, which was purified by flash chromatography using a mixture of ethyl acetate and hexane (1:9) as an eluent to afford 1.96 g (yield 86%) of the title compound as a white solid.

M.p.: 97° to 99° C. $^1$H-NMR(200 MHz, CDCl$_3$) δ 1.04 (3H, t, J=7.5 Hz), 2.33(6H, s), 2.41(2H, q, J=7.5 Hz), 3.93(3H, s), 4.04(3H, s), 7.22(1H, s), 7.45(2H, s)

Step 2) Synthesis of 5-ethyl-6-(3,5-dimethylbenzoyl)-2,4-pyrimidinedione

A solution of 600 mg (2 mmol) of the compound obtained from step 1 in 15 ml of conc. HCl-methanol (1:2) was refluxed with stirring for about 16 hours and evaporated under reduced pressure to give a light yellow residue, which was recrystallized from methanol-chloroform (5:1) to afford 480 mg (yield 88%) of the title compound as a white solid.

M.p.: 249° to 250° C. $^1$H-NMR(200 MHz, CDCl$_3$/CD$_3$OD) δ 0.97(3H, t, J=7.4 Hz), 2.17(2H, q, J=7.4 Hz), 2.39(6H, s), 7.32(1H, s), 7.50(2H, s) m/z(EI) 272(M$^+$, 42%), 257(M—CH$_3^+$, 100%)

Preparation 7

Synthesis of 5-isopropyl-6-(3,5-dimethylbenzyl)-2,4-pyrimidinedione

Step 1) Synthesis of 2,4-dimethoxy-5-isopropyl-6-(α-cyano-3,5-dimethylbenzyl)-1,3-pyrimidine To a stirred solution of 2.9 g (13.4 mmol) of the compound obtained from step 1 of Preparation 3 and 2.32 g (16.1 mmol) of 3,5-dimethylphenylacetonitrile in 26 ml of DMF was added 643 mg (16.1 mmol) of 60% sodium hydride under nitrogen atmosphere. The resulting mixture was stirred for 24 hours at room temperature and neutralized with acetic acid. The mixture was then diluted with ether, washed with water, dried over anhydrous magnesium sulfate, and evaporated under reduced pressure to give a yellow-colored residue, which was purified by flash chromatography using a mixture of ethyl acetate and hexane (1:10) as an eluent to afford 2.33 g (yield 54%) of the title compound as a white solid.

M.p.: 107° to 108° C. $^1$H-NMR(200 MHz, CDCl$_3$) δ 1.11(3H, d, J=7.0 Hz), 1.13(3H, d, J=7.0 Hz), 2.29(6H, s), 3.07(1H, m), 4.00(3H, s), 4.04(3H, s), 5.37(1H, s), 6.94(1H, s), 7.00(2H, s)

Step 2) Synthesis of 5-isopropyl-6-(3,5-dimethylbenzyl)-2,4-pyrimidinedione

A solution of 2.14 g (6.58 mmol) of the compound obtained from step 1 in 20 ml of conc. HCl was heated to reflux, with stirring, for 48 hours and evaporated under reduced pressure to give a yellow-colored residue, which was recrystallized from chloroform-methanol (1:6) to afford 1.0 g (yield 56%) of the title compound as a white solid.

M.p.: 268° to 269° C. $^1$H-NMR(200 MHz, CDCl$_3$/CD$_3$OD) δ 1.24(6H, d, J=7.0 Hz), 2.29(6H, s), 2.94(1H, m), 3.73(2H, s), 6.80(2H, s), 6.91(1H, s) m/z(EI) 272(M$^+$, 79%), 257(M—CH$_3^+$, 100%)

Preparation 8

Synthesis of 5-isopropyl-6-(3,5-dimethylbenzoyl)-2,4-pyrimidinedione

Step 1) Synthesis of 2,4-dimethoxy-5-isopropyl-6-(3,5-dimethylbenzoyl)-1,3-pyrimidine To a stirred solution of 198 mg (0.61 mmol) of the compound obtained from step 1 of Preparation 7 in 6 ml of DMF was added 24 mg (0.63 mmol) of 60% sodium hydride at room temperature under an atmosphere of nitrogen. The resulting mixture was then stirred for about 2 hours under an air atmosphere, diluted with 10 ml of ether, washed with water, dried over anhydrous magnesium sulfate, and evaporated under reduced pressure to give a light yellow-colored residue, which was purified by flash chromatography using a mixture of ethyl acetate and hexane (1:7) as an eluent to afford 190 mg (yield 99%) of the title compound as a white solid.

M.p.: 149° to 150° C. $^1$H-NMR(200 MHz, CDCl$_3$) δ 1.20(6H, d, J=6.9 Hz), 2.37(6H, s), 2.81(1H, m), 3.96(3H, s), 4.08(3H, s), 7.28(1H, s), 7.47(2H, s)

Step 2) Synthesis of 5-isopropyl-6-(3,5-dimethylbenzoyl)-2,4-pyrimidinedione

A solution of 186 mg (0.59 mmol) of the compound obtained from step 1 in 15 ml of conc. HCl-methanol (1:2) was heated to reflux with stirring for about 16 hours and evaporated under reduced pressure to give a light yellow-colored residue, which was recrystallized from chloroform-hexane (1:1) to afford 130 mg (yield 77%) of the title compound as a white solid.

M.p.: 238° to 239° C. $^1$H-NMR(200 MHz, CDCl$_3$/CD$_3$OD) δ 1.16(6H, d, J=6.9 Hz), 2.35–2.49 (7H, m), 7.35(1H, s), 7.53(2H, s) m/z(EI) 286(M$^+$, 100%), 271(M—CH$_3^+$, 32%)

Preparation 9

Synthesis of 5-ethyl-6-(3,5-dimethylphenoxy)-2,4-pyrimidinedione

Step 1) Synthesis of 2,4-dichloro-5-ethyl-6-(3,5-dimethylphenoxy)-1,3-pyrimidine To a stirred solution of 10 g (47.6 mmol) of 5-ethyl-2,4,6-trichloro-1,3-pyrimidine in 150 ml of DMF were added 5.8 g (47.6 mmol) of 3,5-dimethylphenol and 1.9 g (47.6 mmol) of 60% sodium hydride under nitrogen. The resulting mixture was stirred for about 26 hours at room temperature and neutralized with acetic acid. The mixture was then diluted with ether, washed with water, dried over anhydrous magnesium sulfate, and evaporated under reduced pressure to give a yellow-colored residue, which was purified by flash chromatography using a mixture of ethyl acetate and hexane (1:30) as an eluent to afford 13 g (yield 92%) of the title compound as a white solid.

M.p.: 91° to 92° C. $^1$H-NMR(200 MHz, CDCl$_3$) δ 1.25 (3H, t, J=7.5 Hz), 2.35(6H, s), 2.84(2H, q, J=7.5 Hz), 6.74(2H, s), 6.92(1H, s)

Step 2) Synthesis of 5-ethyl-6-(3,5-dimethylphenoxy)-2,4-pyrimidinedione

To a stirred solution of 1.84 g (17 mmol) of benzyl alcohol in 20 ml of toluene was added 0.39 g (17 mmol) of sodium under nitrogen. After stirring for about 6 hours at room temperature, 2.52 g (11.9 mmol) of the compound obtained from step 1 was added and the stirring was continued for another 11 hours at room temperature. The mixture was then evaporated under reduced pressure to give a light yellow residue, which was purified by flash chromatography using a mixture of ethyl acetate and hexane (1:9) as an eluent to afford 2.6 g of 2,4-dibenzyloxy-5-ethyl-6-(3,5-dimethylphenoxy)-1,3-pyrimidine as a colorless oil.

A solution of 2 g (4.5 mmol) of the benzylated compound in 20 ml of ethanol was stirred under an atmosphere of hydrogen in the presence of 10% palladium on charcoal at room temperature for 6 hours. The reaction mixture was filtered through Cellite pad and evaporated under reduced pressure to give a light yellow residue, which was recrystallized from methanol-chloroform to afford 420 mg (yield 36%) of the title compound as a white solid.

M.p.: 221° to 222° C. $^1$H-NMR(200 MHz, CD$_3$OD) δ 0.90(3H, t, J=7.4 Hz), 2.17–2.25(8H, m), 6.62(2H, s), 6.78 (1H, s) m/z(EI) 260(M$^+$, 69%), 245(M—CH$_3^+$, 100%)

Preparation 10

Synthesis of 5-isopropyl-6-(3,5-dimethylphenoxy)-2,4-pyrimidinedione

Step 1) Synthesis of 2,4-dichloro-5-isopropyl-6-(3,5-dimethylphenoxy)-1,3-pyrimidine To a stirred solution of 2.26 g (10 mmol) of 5-isopropyl-2,4,6-trichloro-1,3-pyrimidine in 150 ml of DMF were added 1.28 g (10.5 mmol) of 3,5-dimethylphenol and 420 mg (10.5 mmol) of 60% sodium hydride under nitrogen. The reaction mixture was stirred for about 17 hours at room temperature and neutralized with acetic acid. The mixture was diluted with ether, washed with water, dried over anhydrous magnesium sulfate, and evaporated under reduced pressure to give a light yellow-colored oil, which was purified by flash chromatography using a mixture of ethyl acetate and hexane (1:30) as an eluent to afford 3 g (yield 96%) of the title compound as a white solid.

M.p.: 91° to 92° C. $^1$H-NMR(20 MHz, CDCl$_3$) δ 1.39(6H, d, J=7.1 Hz), 2.33(6H, s), 3.56(1H, m), 6.70(2H, s), 6.89 (1H, s)

Step 2) Synthesis of 5-isopropyl-6-(3,5-dimethylphenoxy)-2,4-pyrimidinedione

To a stirred solution of 2.2 g (20 mmol) of benzyl alcohol in 20 ml of toluene was added 513 mg (22 mmol) of sodium under nitrogen. After stirring for about 5 hours at room temperature, 3 g (9.7 mmol) of the compound obtained from step 1 was added and the stirring was continued for another 10 hours at room temperature. The mixture was then evaporated under reduced pressure to give a light yellow residue, which was purified by flash chromatography using a mixture of ethyl acetate and hexane (1:9) as an eluent to afford 3 g of 2,4-dibenzyloxy-5-isopropyl-6-(3,5-dimethylphenoxy)-1,3-pyrimidine as a colorless oil.

A solution of 2.8 g (6.17 mmol) of the benzylated compound in 20 ml of ethanol was stirred under an atmosphere of hydrogen in the presence of 10% palladium on charcoal at room temperature for 5 hours. The reaction mixture was filtered through Cellite pad and evaporated under reduced pressure to give a light yellow residue, which was recrystallized from methanol-chloroform to afford 1.06 g (yield 63%) of the title compound as a white solid.

M.p.: 229° to 230° C. $^1$H-NMR(200 MHz, CD$_3$OD) δ 1.20(6H, d, J=7.1 Hz), 2.33(6H, s), 3.35(1H, m), 6.64(2H, s), 6.83(1H, s)

EXAMPLE 1

Synthesis of 1-propargyl-5-ethyl-6-phenylthio-2,4-pyrimidinedione

To a stirred solution of 248 mg (1 mmol) of the compound obtained from Preparation 1 and 138 mg (1 mmol) of anhydrous potassium carbonate in 5 ml of DMF was added 130 μl (1.2 mmol) of propargyl bromide. The reation mixture was stirred for about 24 hours at room temperature and evaporated under reduced pressure to give a yellow residue, which was purified by flash chromatography using a mixture of ethyl acetate and hexane (1:2) as an eluent to afford 120 mg (yield 42%) of the title compound as a white solid.

M.p.: 132° C. $^1$H-NMR(200 MHz, CDCl$_3$) δ 1.10(3H, t, J=7.5 Hz), 2.21(1H, t, J=2.4 Hz), 2.27(2H, q, J=7.5 Hz), 4.82(2H, d, J=2.4 Hz), 7.25–7.43(5H, m), 9.49(1H, s) IR(KBr) 3200(w, NH), 1700, 1650 cm$^{-1}$(s, CO)

EXAMPLE 2

Synthesis of 1-(trans-2-pentenyl)-5-ethyl-6-(3,5-dimethylphenylthio)-2,4-pyrimidinedione To a stirred solution of 166 mg (0.6 mmol) of the compound obtained from Preparation 2 and 83 mg (0.6 mmol) of anhydrous potassium carbonate in 5 ml of DMF was added 89 μl (0.6 mmol) of 1-bromo-2-pentene. The reaction mixture was stirred at room temperature for about 24 hours and then evaporated under reduced pressure to give a yellow residue, which was purified by flash chromatography using a mixture of ethyl acetate and hexane (1:2) as an eluent to afford 178 mg (yield 86%) of the title compound as a white solid.

M.p.: 129° to 130° C. $^1$H-NMR(200 MHz, CDCl$_3$) δ 0.91(3H, t, J=7.5 Hz), 1.04(3H, t, J=7.5 Hz), 1.94(2H, q, J=7.5 Hz), 2.28(6H, s), 2.70(2H, q, J=7.5 Hz), 4.54–4.59 (2H, m), 5.31–5.68(2H, m), 6.76(2H, s), 6.87(1H, s), 8.90 (1H, s)

EXAMPLE 3

Synthesis of 1-(3-phenyl-2-propynyl)-5-isopropyl-6-(3,5-dimethylphenylthio)-2,4-pyrimidinedione To a stirred solution of 203 mg (0.7 mmol) of the compound obtained from Preparation 3 in 5 ml of DMF were added 110 mg (0.8 mmol) of anhydrous potassium carbonate, 116 mg (0.8 mmol) of 1-chloro-3-phenyl-2-propyn, and 471 mg (0.35 mmol) of lithium iodide. The reaction mixture was stirred for about 16 hours at room temperature and evaporated under reduced pressure to give a light yellow-colored residue, which was purified by flash chromatography using a mixture of ethyl acetate and hexane (1:3) as an eluent to afford 156 mg (yield 55%) of the title compound as a white solid.

M.p.: 113° to 115° C. $^1$H-NMR(200 MHz, CDCl$_3$) δ 1.22(6H, d, J=7.0 Hz), 2.22(6H, s), 3.50 (1H, m), 5.06(2H, s), 6.82(1H, s), 6.86(2H, s); 7.19–7.31(5H, m), 8.77(1H, s)

EXAMPLE 4

Synthesis of 1-allyl-5-ethyl-6-benzyl-2,4-pyrimidinedione

To a stirred solution of 460 mg (2 mmol) of the compound obtained from Preparation 4 and 276 mg (2 mmol) of anhydrous potassium carbonate in 10 ml of DMF was added 174 μl (2 mmol) of allyl bromide at room temperature. After 48 hours, the mixture was evaporated under reduced pressure to give a yellow-colored residue, which was purified by flash chromatography using a mixture of ethyl acetate and hexane (2:5) as an eluent to afford 35 mg (yield 6%) of the title compound as a white solid.

M.p.: 164° to 165° C. $^1$H-NMR(200 MHz, CDCl$_3$) δ 1.06(3H, t, J=7.5 Hz), 2.48(2H, q, J=7.5 Hz), 3.99(2H, s), 4.28–4.31(2H, m), 5.04–5.24(2H, m), 5.85(1H, m), 7.09–7.41(5H, m), 9.37(1H, s)

EXAMPLE 5

Synthesis of 1-(trans-2-butenyl)-5-ethyl-6-(3,5-dimethylbenzyl)-2,4-pyrimidinedione To a stirred solution of 258 mg (1 mmol) of the compound obtained from Preparation 5 in 5 ml of DMF were added 138 mg (1 mmol) of anhydrous potassium carbonate and 121 μl (1 mmol) of 85% trans-crotyl bromide at room temperature. After 45 hours, the reaction mixture was then evaporated under reduced pressure to give a yellow-colored residue, which was purified by flash chromatography using a mixture of ethyl acetate and hexane (1:1) as an eluent to afford 43 mg (yield 14%) of the title compound as a white solid.

M.p.: 145° to 146° C. $^1$H-NMR(200 MHz, CDCl$_3$) δ 1.06(3H, t, J=7.5 Hz), 1.70(3H, d, J=5.1 Hz), 2.30(6H, s), 2.46(2H, q, J=7.5 Hz), 3.92(6H, s), 4.20–4.23 (2H, m), 5.48–5.62(2H, m), 6.69(2H, s), 6.91(1H, s), 9.23(1H, s)

EXAMPLE 6

Synthesis of 1-(trans-cinnamyl)-5-isopropyl-6-(3,5-dimethylbenzyl)-2,4-pyrimidinedione To a stirred solution of 408 mg (1.5 mmol) of the compound obtained from Preparation 7 in 5 ml of DMF were added 248 mg (1.8 mmol) of anhydrous potassium carbonate and 296 mg (1.5 mmol) of cinnamyl bromide at room temperature. After 36 hours, the reaction mixture was then evaporated under reduced pressure to give a yellow-colored residue, which was purified by flash chromatography using a mixture of ethyl acetate and hexane (1:2) as an eluent to afford 88 mg (yield 15%) of the title compound as a white solid.

M.p.: 180° to 181° C. $^1$H-NMR(200 MHz, CDCl$_3$) δ 1.31(6H, d, J=7.0 Hz), 2.31(6H, s), 2.85 (1H, m), 3.99(2H, s), 4.47(2H, d, J=4.4 Hz), 6.17(1H, m), 6.40 (1H, d, J=16.1 Hz), 6.73(2H, s), 6.93(1H, s), 7.22–7.40(5H, m), 8.79(1H, s)

EXAMPLE 7

Synthesis of 1-(3-methyl-2-butenyl)-5-ethyl-6-(3,5-dimethylbenzoyl)-2,4-pyrimidinedione To a stirred solution of 272 mg (1 mmol) of the compound obtained from Preparation 6 in 5 ml of DMF were added 138 mg (1 mmol) of anhydrous potassium carbonate and 115 μl (1 mmol) of 1-bromo-3-methyl-2-butene at room temperature. After 16 hours; the reaction mixture was evaporated under reduced pressure to give a yellow-colored residue, which was purified by flash chromatography using a mixture of ethyl acetate and hexane (1:2) as an eluent to afford 248 mg (yield 72%) of the title compound as a white solid.

M.p.: 255° to 260° C. $^1$H-NMR(200 MHz, CDCl$_3$) δ 0.96(3H, t, J=7.4 Hz), 1.37(3H, s), 1.46 (3H, s), 2.03(1H,m), 2.26(1H,m), 2.40(6H, s), 4.23–4.27(2H, m), 4.99(1H, m), 7.33(1H, s), 7.52(2H, s), 8.71(1H, s)

EXAMPLE 8

Synthesis of 1-(methoxycarbonylallyl)-5-ethyl-6-(3, 5-dimethylbenzoyl)-2,4-pyrimidinedione To a stirred solution of 272 mg (1 mmol) of the compound obtained from Preparation 6 and 138 mg (1 mmol) of anhydrous potassium carbonate in 5 ml of DMF was added 138 μl (1 mmol) of 85% methyl 4-bromocrotonate at room temperature. After 4 hours, the reaction mixture was evaporated under reduced pressure to give a yellow-colored residue, which was purified by flash chromatography using a mixture of ethyl acetate and hexane (3:1) as an eluent to afford 151 mg (yield 41%) of the title compound as a white solid.

M.p.: 201° to 202° C. $^1$H-NMR(200 MHz, CDCl$_3$) δ 0.96(3H, t, J=7.4 Hz), 2.00–2.31(2H, m), 2.37(6H, s), 3.67 (3H, s), 4.22–4.38(2H, m), 5.69(1H, m), 6.67 (1H, m), 7.32(1H, s), 7.49(2H, s)

EXAMPLE 9

Synthesis of 1-(4-chloro-trans-2-butenyl)-5-isopropyl-6-(3,5-dimethylbenzoyl)-2,4-pyrimidinedione To a stirred solution of 1.43 g (5 mmol) of the compound obtained from Preparation 8 in 10 ml of DMF were added 690 mg (5 mmol) of anhydrous potassium carbonate and 525 μl (5 mmol) of 1,4-dichloro-trans-2-butene at room temperature. After 42 hours, the reaction mixture was diluted with ether, washed with water, dried over anhydrous magnesium sulfate, and evaporated under reduced pressure to give a yellow-colored residue, which was purified by flash chromatography using a mixture of ethyl acetate and hexane (1:2) as an eluent to afford 860 mg (yield 46%) of the title compound as a white solid.

M.p.: 178° to 179° C. $^1$H-NMR(200 MHz, CDCl$_3$) δ 1.12(3H, d, J=6.9 Hz), 1.20(3H, d, J=6.9 Hz), 2.31(1H, m), 2.39(6H, s), 3.83(2H, d, J=6.5 Hz), 4.08(1H, m), 4.25(1H, m), 5.46–5.72(2H, m), 7.33(1H, s), 7.51(2H, s), 9.41(1H, s)

EXAMPLE 10

Synthesis of 1-(trans-2-butenyl)-5-ethyl-6-(3,5-dimethylphenoxy)-2,4-pyrimidinedione To a stirred solution of 260 mg (1 mmol) of the compound obtained from Preparation 9 in 5 ml of DMF were added 138 mg (1 mmol) of anhydrous potassium carbonate and 121 μl (1 mmol) of 85% trans-crotyl bromide at room temperature. After 16 hours, the reaction mixture was evaporated under reduced pressure to give a yellow-colored residue, which was purified by flash chromatography using a mixture of ethyl acetate and hexane (1:2) as an eluent to afford 188 mg (yield 60%) of the title compound as a white solid.

M.p.: 149° to 150° C. $^1$H-NMR(200 MHz, CDCl$_3$) δ 0.94(3H, t, J=7.5 Hz), 1.61(2H, d, J=6.0 Hz), 2.14–2.30(8H, m), 4.23–4.26(2H, m), 5.40–5.60(2H, m), 6.53(2H, s), 6.77 (1H, s), 8.88 (1H, s)

EXAMPLE 11

Synthesis of 1-(2-butynyl)-5-isopropyl-6-(3,5-dimethylphenoxy)-2,4-pyrimidinedione To a stirred solution of 274 mg (1 mmol) of the compound obtained from Preparation 10 in 5 ml of DMF were added 152 mg (1.1 mmol) of anhydrous potassium carbonate and 163 mg (1.1 mmol) of 1-methylsulfonyl-2-butyn at room temperature. After 15 hours, the reaction mixture was diluted with ether, washed with water, dried over anhydrous magnesium sulfate, and evaporated under reduced pressure to give a yellow-colored residue, which was purified by flash chromatography using a mixture of ethyl acetate and hexane (1:4) as an eluent to afford 175 mg (yield 54%) of the title compound as a white solid.

M.p.: 158° to 160° C. $^1$H-NMR(200 MHz, CDCl$_3$) δ 1.15(6H, d, J=7.1 Hz), 1.69(3H, t, J=2.2 Hz), 2.32(6H, s), 2.80(1H, m), 3.73(3H, s), 4.43(2H, q, J=2.2 Hz), 6.60(2H, s), 6.78(1H, s), 8.55(1H, s)

Similarly to Examples above, various 2,4-pyrimidinedione derivatives of the present invention were prepared and a list of them is represented in Table 1.

TABLE 1

| Ex. No. | R$^1$ | R$^2$ | R$^3$ | R$^4$ | Z | $^1$H-NMR(200MHz, CDCl$_3$)δ | M.P. (°C.) |
|---|---|---|---|---|---|---|---|
| 12 | CH$_2$=CH—CH$_2$— | CH$_3$CH$_2$— | H | H | S | 1.02(3H, t, J=7.5Hz), 2.70 (2H, q, J=7.5Hz), 4.58–4.62(2H, m), 5.03–5.15(2H, m), 7.14–7.38 (5H, m), 9,49(1H, s) | 133–134 |
| 13 | trans CH$_3$CH=CH—CH$_2$— | CH$_3$CH$_2$— | H | H | S | 1.01(3H, t, J=7.4Hz), 1.57 (3H, dd, J=1.2Hz, 6.2Hz), 2.68(2H, q, J=7.4Hz), 4.50–4.59(2H, m), 5.25–5.65 (2H, m), 7.10–7.36(5H, m), 9.28(1H, s) | 132–133 |
| 14 | trans PhCH=CH—CH$_2$— | CH$_3$CH$_2$— | H | H | S | 1.04(3H, t, J=7.5Hz), 2.72 (3H, q, J=7.5Hz), 4.74–4.77(2H, m), 5.91–6.11 (2H, m), 6.46(1H, d, J=15.9Hz), 7.15–7.38(10H, | 180–181 |

TABLE 1-continued

| Ex. No. | R¹ | R² | R³ | R⁴ | Z | ¹H-NMR(200MHz, CDCl₃)δ | M.P. (°C.) |
|---|---|---|---|---|---|---|---|
| | | | | | | m), 9.37(1H, s) | |
| 15 | (CH₃)₂C=CH—CH₂— | CH₃CH₂— | H | H | S | 1.04(3H, t, J=7.4Hz), 1.61 (3H, s), 1.67(3H, s), 2.70 (2H, q, J=7.4Hz), 4.56– 4.59(2H, m), 4.98-5.05(1H, m), 7.13-7.38(5H, m), 9.24 (1H, s) | 162–163 |
| 16 | cis CH₃CH₂OCH₂CH=CH —CH₂— | CH₃CH₂— | H | H | S | 1.02(3H, t, J=7.4Hz), 1.16 (3H, t, J=7.0Hz), 2.69(2H, q, J=7.4Hz), 3.45(2H, q, J=7.0Hz), 4.05(2H, dd, J= 1.4Hz, 6.2 Hz), 4.62(2H, m), 5.35(1H, m), 5.64(1H, m), 7.13-7.38(5H, m), 8.89(1H, s) | 103–104 |
| 17 | cis PhCH₂OCH₂CH=CH— CH₂— | CH₃CH₂— | H | H | S | 1.03(3H, s, J=7.5Hz), 2.69 (2H, q, J=7.5Hz), 4.13(1H, m), 4.49 (2H, s), 4.61(2H, m), 5.40(1H, m), 5.67(1H, m), 7.08-7.36(10H, m), 8.98(1H, s) | 105–106 |
| 18 | CH₂=CH—CH₂— | CH₃CH₂— | CH₃ | CH₃ | S | 1.04(3H, t, J=7.5Hz), 2.28 (6H, s), 2.70(2H, q, J= 7.5Hz), 4.58-4.61(2H, m), 5.03-5.17(2H, m), 5.75(1H, m), 6.75(2H, s), 6.87(1H, s), 9.40(1H, s) | 164–165 |
| 19 | trans CH₃CH=CH—CH₂— | CH₃CH₂— | CH₃ | CH₃ | S | 1.04(3H, t, J=7.5Hz), 1.62 (3H, dd, J=1.3Hz, 6,2Hz), 2.29(6H, s), 2,70(2H, q, J=7.5Hz), 4.52-4.55(2H, m), 5.37-5.66(2H, m), 6.76 (2H, s), 6.88(1H, s), 9.08 (1H, s) | 158–159 |
| 20 | trans PhCH=CH— CH₂— | CH₃CH₂— | CH₃ | CH₃ | S | 1.03(3H, t, J=7.4Hz), 2.23 (6H, s), 2.70(2H, q, J=7.5 Hz), 4.73-4.76 (2H, m), 6.04-6.10(1H, m), 6.42(1H, d, J=15.8 Hz), 6.78(2H, s), 6.82 (1H, s), 7.22(5H, m), 9.11(1H, s) | 160–162 |
| 21 | trans CH₃O₂CCH=CH— CH₂— | CH₃CH₂— | CH₃ | CH₃ | S | 1.06(3H, t, J=7.3Hz), 2.26 (6H, s), 2.70(2H, q, J=7.3 Hz), 3.68(3H, s), 4.73(2H, dd, J=1.7 Hz, 5.0Hz), 5.62 (1H, m), 6.67(1H, m), 6.75 (2H, s), 6.85(1H, s), 9.07 (1H, s) | 210–211 |
| 22 | trans ClCH₂CH=CH—CH₂— | CH₃CH₂— | CH₃ | CH₃ | S | 1.04(3H, t, J=7.3Hz), 2.27 (6H, s), 2.70(2H, q, J=7.3 Hz), 3.91-3.93(2H, m), 4.58-4.60(2H, m), 5.64– 5.69(2H, m), 6.75(2H, m), 6.87(1H, s), 8.86(1H, s) | 164 |
| 23 | cis ClCH₂CH=CH—CH₂— | CH₃CH₂— | CH₃ | CH₃ | S | 1.08(3H, t, J=7.4Hz), 2.28 (6H, s), 2,71(2H, q, J=7.4 Hz), 4.15(2H, d, J=7.3Hz), 4.64(2H, d, J=7.3Hz), 5.42 (1H, m), 5.71(1H, m), 6.75 (2H, s), 6.88(1H, s), 9.82 (1H, s) | 152–153 |
| 24 | HC≡CCH₂— | CH₃CH₂— | CH₃ | CH₃ | S | 1.06(3H, t, J=7.5Hz), 2.20 (1H, t, J=2.4Hz), 2.29(6H, s), 2.73(2H, q, J=7.5Hz), 4.76(2H, d, J=2.4Hz), 6.82 (2H, s), 6.90(1H, s), 9.44 (1H, s) | 180–181 |
| 25 | H₃CC≡CCH₂— | CH₃CH₂— | CH₃ | CH₃ | S | 1.03(3H, t, J=7.5Hz), 1.69 (3H, t, J=2.4Hz), 2.27(6H, s), 2.70(2H, q, J=7.5Hz), 4.70-4.72 (2H, m), 6.81 (2H, s), 6.86(1H, s), 9.74 (1H, s) | 186–187 |
| 26 | PhC≡CCH₂— | CH₃CH₂— | CH₃ | CH₃ | S | 1.03(3H, t, J=7.4Hz), 2.22 (6H, s), 2.70(2H, q, J=7.4 Hz), 5.00(2H, s), 6.82– 7.33(8H, m), 8.95(1H, s) | 178–180 |

TABLE 1-continued

| Ex. No. | R¹ | R² | R³ | R⁴ | Z | ¹H-NMR(200MHz, CDCl₃)δ | M.P. (°C.) |
|---|---|---|---|---|---|---|---|
| 27 | trans CH₃CH=CH—CH₂— | (CH₃)₂CH— | CH₃ | CH₃ | S | 1.22(6H, d, J=7.0Hz), 1.61–1.67(3H, m), 2.26 (6H, s), 3.50(1H, m), 3.58–4.60 (2H, m), 5.40–5.67(2H, m), 6.76(2H, s), 6.87(1H, s) | 166–167 |
| 28 | trans CH₃CH₂CH=CH—CH₂— | (CH₃)₂CH— | CH₃ | CH₃ | S | 0.89(3H, t, J=7.5Hz), 1.21 (6H, d, J=7.0Hz),1.87–2.02 (2H, m), 2.25 (6H, s), 3.47(1H, m), 4.61(2H, d, J=5.2Hz), 5.40(1H, m), 5.64(1H, m), 6.74(2H, s), 6.84 (1H, s), 10.14(1H, s) | 122—123 |
| 29 | trans PhCH=CH—CH₂— | (CH₃)₂CH— | CH₃ | CH₃ | S | 1.23(6H, d, J=6.7Hz), 2.23 (6H, s), 3.52(1H, m), 4.80–4.83(2H, m), 6.09(1H, m), 6.46(1H, d, J=15.9Hz), 6.79(2H, s), 6.83(1H, s), 7.17–7.25(5H, m) | 133–134 |
| 30 | trans CH₃O₂CCH=CH—CH₂— | (CH₃)₂CH— | CH₃ | CH₃ | S | 1.29(6H, d, J=7.0Hz), 2.29 (6H, s), 3.56(1H, m), 3.71 (3H, s), 4.78–4.82(2H, m), 5.68(1H, m), 6.83–6.87 (4H, m) | 147–148 |
| 31 | H₃CC≡CCH₂— | (CH₃)₂CH— | CH₃ | CH₃ | S | 1.24(6H, d, J=7.0Hz), 1.72 (3H, t, J=2.3Hz), 2.30(6H, s), 3.51(1H, m), 4.78–4.81 (2H, m), 6.85 (2H, s), 6.89(1H, s), 8.87(1H, s) | 165–166 |
| 32 | trans CH₃CH=CH—CH₂— | CH₃CH₂— | H | H | CH₂ | 1.06(3H, t, J=7.4Hz), 1.69 (3H, d, J=4.8Hz), 2.47(2H, q, J=7.4Hz), 4.01(2H, s), 4.21–4.23(2H, m), 5.47–5.54(2H, m), 7.10–7.40(5H, m), 9.10(1H, s) | 132–133 |
| 33 | trans PhCH=CH—CH₂— | CH₃CH₂— | H | H | CH₂ | 1.05(3H, t, J=7.4Hz), 2.48 (2H, q, J=7.4Hz), 4.03(2H, s), 4.42–4.45(2H, m), 6.12 (1H, m), 6.38(1H, d, J=15.1Hz), 7.12–7.44(10H, m), 9.38(1H, s) | 159–160 |
| 34 | CH₂=CH—CH₂— | CH₃CH₂— | CH₃ | CH₃ | CH₂ | 1.09(3H, t, J=7.5Hz), 2.28 (6H, s), 2.51(2H, q, J=7.5 Hz), 3.71 (2H, s), 4.49 (2H, dd, J=1.3Hz, 5.8 Hz), 5.12–5.27(2H, m), 5.85(1H, m), 6.80 (2H, s), 6.92(1H, s), 8.55(1H, s) | 129–130 |
| 35 | trans PhCH=CH—CH₂— | CH₃CH₂— | CH₃ | CH₃ | CH₂ | 1.07(3H, t, J=7.4Hz), 2.31 (6H, s), 2.48(2H, q, J=7.4 Hz), 3.97 (2H, s), 4.44–4.47(2H, m), 6.09–6.43(2H, m), 6.73(2H, s), 6.93 (1H, s), 7.25–7.34(5H, m), 8.26 (1H, s) | 223–224 |
| 36 | (CH₃)₂C=CH—CH₂— | CH₃CH₂— | CH₃ | CH₃ | CH₂ | 1.07(3H, t, J=7.5Hz), 1.64 (3H, s), 1.72(3H, s), 2.30 (6H, s), 2.46 (2H, q, J=7.5Hz), 3.91 (2H, s), 4.28 (2H, d, J=6.2Hz), 5.08 (1H, m), 6.70(2H, s), 6.92 (1H, s), 9.46(1H, s) | 169–170 |
| 37 | trans CH₃O₂CCH=CH—CH₂— | CH₃CH₂— | CH₃ | CH₃ | CH₂ | 1.11(3H, t, J=7.5Hz), 2.30 (6H, s), 2.52(2H, q, J=7.5 Hz), 3.71(3H, s), 3.73(2H, s), 4.63–4.67(2H, m), 5.89 (1H, m), 6.81–6.95(4H, m), 8.13(1H, s) | 105–106 |
| 38 | HC≡CCH₂— | CH₃CH₂— | CH₃ | CH₃ | CH₂ | 1.07(3H, t, J=7.5Hz), 2.28 (6H, s), 2.34(1H, t, J=2.4 Hz), 2.48(2H, q, J=7.5Hz), 4.08(2H, s), 4.42(2H, d, J=2.4 Hz), 6.70(2H, s), 6.90(1H, s), 9.03(1H, s) | 163–164 |
| 39 | H₃CC≡CCH₂— | CH₃CH₂— | CH₃ | CH₃ | CH₂ | 1.08(3H, t, J=7.5Hz), 1.82 (3H, t, J=2.3Hz), 2.39(6H, s), 2.45(2H, q, J=7.5Hz), 4.09(2H, s), 4.38(2H, d, | 179–180 |

TABLE 1-continued

| Ex. No. | $R^1$ | $R^2$ | $R^3$ | $R^4$ | Z | $^1$H-NMR(200MHz, CDCl$_3$)$\delta$ | M.P. (°C.) |
|---|---|---|---|---|---|---|---|
| 40 | PhC≡CCH$_2$— | CH$_3$CH$_2$— | CH$_3$ | CH$_3$ | CH$_2$ | J=8.4 Hz), 6.72(2H, s), 6.90 (1H, s), 9.40(1H, s) 1.09(3H, t, J=7.5Hz), 2.29 (6H, s), 2.50(2H, q, J= 7.5Hz), 4.16(2H, s), 4.67 (2H, s), 6.75 (2H, s), 6.91(1H, s), 7.01–7.60(5H, m), 9.51 (1H, s) | 187–189 |
| 41 | trans CH$_3$CH=CH—CH$_2$— | (CH$_3$)$_2$CH— | CH$_3$ | CH$_3$ | CH$_2$ | 1.28(6H, d, J=7.0Hz), 1.70 (3H, d, J=4.8Hz), 2.29 (6H, s), 2.83(1H, m), 3.92(2H, s), 4.22 (2H, s), 5.48–5.56(2H, m), 6.69(2H, s), 6.91 (1H, s), 8.77(1H, s) | 187–188 |
| 42 | PhC≡CCH$_2$— | (CH$_3$)$_2$CH— | CH$_3$ | CH$_3$ | CH$_2$ | 1.32(6H, d, J=7.0Hz), 2.31 (6H, s), 2.89(1H, m), 4.20 (2H, s), 4.69(2H, s), 6.77(2H, s), 6.93(1H, s), 7.27–7.48 (5H, m) | 149–150 |
| 43 | CH$_2$=CH—CH$_2$— | CH$_3$CH$_2$— | CH$_3$ | CH$_3$ | O‖C | 0.97(3H, t, J=7.4Hz), 2.07 (1H, m), 2.29(1H, m), 2.39(6H, s), 3.98 (1H, m), 4.37(1H, m), 4.98–5.13(2H, m), 5.69 (1H, m), 7.34(1H, s), 7.52(2H, s), 9.42(1H, s) | 177–178 |
| 44 | trans CH$_3$CH=CH—CH$_2$— | CH$_3$CH$_2$— | CH$_3$ | CH$_3$ | O‖C | 0.98(3H, t, J=7.4Hz), 1.51 (3H, d, J=4.8Hz), 1.97– 2.36(2H, m), 2.42(6H, s), 4.03–4.25(2H, m), 5.35– 5.49(2H, m), 7.34(1H, s), 7.53(2H, s), 9.69(1H, s) | 151–152 |
| 45 | trans PhCH=CH— CH$_2$— | CH$_3$CH$_2$— | CH$_3$ | CH$_3$ | O‖C | 0.95(3H, t, J=7.4Hz), 1.97– 2.27(8H, m), 4.21–4.47 (2H, m), 5.97(1H, m), 6.16 (1H, d, J=16.0Hz), 7.07– 7.49(8H, m), 8.99(1H, s) | 171–172 |
| 46 | trans CH$_3$CH$_2$CH=CH— CH$_2$— | CH$_3$CH$_2$— | CH$_3$ | CH$_3$ | O‖C | 0.80(3H, t, J=7.5Hz), 0.95 (3H, t, J=7.5Hz),1.84(2H, q, J=7.5Hz), 2.04(1H, m), 2.29(1H, m), 2.39(6H, s), 4.14 (2H, m), 5.24–5.49 (2H, m), 7.32(1H, s), 7.50 (2H, s), 9.14(1H, s) | 163–164 |
| 47 | trans ClCH$_2$CH=CH—CH$_2$— | CH$_3$CH$_2$— | CH$_3$ | CH$_3$ | O‖C | 0.95(3H, t, J=7.5Hz), 2.04 (1H, m), 2.30(1H, m), 2.39 (6H, s), 3.84 (2H, d, J= 5.3Hz), 4.15 (2H, m), 5.60 (2H, m), 7.33(1H, s), 7.50 (2H, s), 9.03(1H, s) | 158–159 |
| 48 | HC≡CCH$_2$— | CH$_3$CH— | CH$_3$ | CH$_3$ | O‖C | 0.96(3H, t, J=7.4Hz), 2.03– 2.34(3H, m), 2.40 (6H, s), 4.36–4.45(2H, m), 7.35(1H, s), 7.60(2H, s), 9.19(1H, s) | 214–215 |
| 49 | H$_3$CC≡CCH$_2$— | CH$_3$CH$_2$— | CH$_3$ | CH$_3$ | O‖C | 0.92(3H, t, J=7.3Hz), 1.44 (3H, t, J=2.3Hz), 1.96– 2.28(2H, m), 2.37 (6H, s), 4.12(1H, m), 4.59(1H, m), 7.29(1H, s), 7.58(2H, s), 9.85 (1H, s) | 202–203 |
| 50 | PhC≡CCH$_2$— | CH$_3$CH$_2$— | CH$_3$ | CH$_3$ | O‖C | 0.95(3H, t, J=7.4Hz), 2.06– 2.25(8H, m), 4.40 (1H, d, J=17.9Hz), 5.09 (1H, d, J= 17.9Hz), 6.98–7.30(6H, m), 7.61(2H, s), 9.42(1H, s) | 194–195 |
| 51 | trans CH$_3$CH=CH—CH$_2$— | (CH$_3$)$_2$CH— | CH$_3$ | CH$_3$ | O‖C | 1.14(3H, d, J=6.8Hz), 1.23 (3H, d, J=6.8Hz), 1.50 (3H, d, J=4.9Hz), 2.27– 2.42(7H, m), 3.99–4.24 (2H, m), 5.25–5.47(2H, m), 7.35(1H, s), 7.55(2H, s), 8.96(1H, s) | 195–196 |
| 52 | trans PhCH=CH— CH$_2$— | (CH$_3$)$_2$CH— | CH$_3$ | CH$_3$ | O‖C | 1.14(3H, d, J=6.8Hz), 2.24 (3H, d, J=6.8Hz), 2.29– 2.39(7H, m), 4.28–4.51 | 187–189 |

TABLE 1-continued

| Ex. No. | R¹ | R² | R³ | R⁴ | Z | ¹H-NMR(200MHz, CDCl₃)δ | M.P. (°C.) |
|---|---|---|---|---|---|---|---|
| | | | | | | (2H, m), 5.98(1H, m), 6.16 (1H, d, J=16.0Hz), 7.08–7.27(6H, m), 7.53 (2H, s), 9.74(1H, s) | |
| 53 | trans CH₃CH₂CH=CH—CH₂— | (CH₃)₂CH— | CH₃ | CH₃ | O‖C | 0.78(3H, t, J=7.5Hz), 1.11 (3H, d, J=6.8Hz), 1.20(3H, d, J=6.8Hz), 1.73–1.88(2H, m), 2.30 (1H, m), 2.38(6H, s), 4.11(2H, d, J=6.2Hz), 5.20–5.43(2H, m), 7.31 (1H, s), 7.51(2H, s), 8.59 (1H, s) | 168–169 |
| 54 | trans CH₃O₂CCH=CH—CH₂— | (CH₃)₂CH— | CH₃ | CH₃ | O‖C | 1.15(3H, d, J=6.9Hz), 1.22 (3H, d, J=6.9Hz), 2.28–2.39(7H, m), 3.68 (3H, s), 4.11–4.45(2H, m), 5.70(1H, m), 6.66 (1H, m), 7.50(1H, s), 7.52(2H, s), 8.65(1H, s) | 188–189 |
| 55 | H₃CC≡CCH₂— | (CH₃)₂CH— | CH₃ | CH₃ | O‖C | 1.11(3H, d, J=6.8Hz), 1.19 (3H, d, J=6.8Hz), 1.45(3H, t, J=2.4Hz), 2.26–2.40 (7H, m), 4.15(1H, m), 4.61 (1H, m), 7.31(1H, s), 7.61 (2H, s), 8.82 (1H, s) | 191–192 |
| 56 | PhC≡CCH₂— | (CH₃)₂CH— | CH₃ | CH₃ | O‖C | 1.11(3H, d, J=6.8Hz), 1.20 (3H, d, J=6.8Hz), 2.25–2.37(7H, m), 4.36 (1H, d, J=17.9Hz), 5.05 (1H, d, J=17.9Hz), 6.95–7.28(6H, m), 7.62 (2H, s), 8.75(1H, s) | 183–185 |
| 57 | CH₂=CH—CH₂— | CH₃CH₂— | CH₃ | CH₃ | O | 0.94(3H, t, J=7.4Hz), 2.16–2.30(8H, m), 4.31–4.34 (2H, m), 5.09–5.18(2H, m), 5.79(1H, m), 6.54(2H, s), 6.77(1H, s), 9.32 (1H, s) | 184–186 |
| 58 | CH₃C≡C—CH₂— | CH₃CH₂— | CH₃ | CH₃ | O | 0.94(3H, t, J=7.5Hz), 1.69 (3H, t, J=2.4Hz), 2.22 (2H, q, J=7.5Hz), 4.49(2H, q, J=2.4Hz), 6.62(2H, s), 6.79 (1H, s), 8.93(1H, s) | 152–154 |
| 59 | trans PhCH=CH—CH₂— | CH₃CH₂— | CH₃ | CH₃ | O | 0.94(3H, t, J=7.5Hz), 2.16–2.25(8H, m), 4.47–4.50 (2H, m), 6.12(1H, m), 6.38 (1H, d, J=15.8Hz), 6.55 (2H, s), 6.42(1H, s), 7.20–7.30(5H, m), 9.39(1H, s) | 174–175 |
| 60 | HC≡CCH₂— | CH₃CH₂— | CH₃ | CH₃ | O | 0.96(3H, t, J=7.4Hz), 2.19–2.33(9H, m), 4.54 (2H, d, J=2.4Hz), 6.63(2H, s), 6.81(1H, s), 9.04(1H, s) | 178–179 |
| 61 | PhC≡CCH₂— | CH₃CH₂— | CH₃ | CH₃ | O | 0.93(3H, t, J=7.4Hz), 2.15–2.24(8H, m), 4.78(2H, s), 6.65(2H, s), 6.75(1H, s), 7.20–7.29(5H, m), 8.79 (1H, s) | 128–129 |
| 62 | trans CH₃CH₂CH=CH—CH₂— | CH₃CH₂— | CH₃ | CH₃ | O | 0.87–0.99(6H, m), 1.98(2H, q, J=7.4Hz), 2.21 (2H, q, J=7.4Hz), 2.31 (6H, s), 4.25–4.30(2H, m), 5.31–5.65(2H, m), 6.55(2H, s), 6.78(1H, s), 8.25(1H, s) | 145–146 |
| 63 | trans CH₃O₂CCH=CH—CH₂— | CH₃CH₂— | CH₃ | CH₃ | O | 0.96(3H, t, J=7.4Hz), 2.17–2.73(8H, m), 3.73(3H, s), 4.46–4.49(2H, m), 5.83(1H, m), 6.53 (2H, s), 6.77–6.85 (2H, m) | 188–189 |
| 64 | trans CH₃CH=CH—CH₂— | (CH₃)₂CH— | CH₃ | CH₃ | O | 1.13(6H, d, J=7.0Hz), 1.59 (3H, d, J=5.0Hz), 2.29(6H, s), 2.78(1H, m), 4.20(2H, d, J=5.5Hz), 5.34–5.61(2H, m), 6.51(2H, s), 6.75(1H, s), 8.75(1H, s) | 141–143 |
| 65 | trans PhCH=CH—CH₂— | (CH₃)₂CH— | CH₃ | CH₃ | O | 1.15(6H, d, J=7.0Hz), 2.27 (6H, s), 2.79 (1H, m), 4.46 (2H, d, J=6.2 Hz), 6.11 (1H, m), 6.37 (1H, d, J= | 157–158 |

TABLE 1-continued

| Ex. No. | R¹ | R² | R³ | R⁴ | Z | ¹H-NMR(200MHz, CDCl₃)δ | M.P. (°C.) |
|---|---|---|---|---|---|---|---|
| 66 | trans CH₃O₂CCH=CH—CH₂— | (CH₃)₂CH— | CH₃ | CH₃ | O | 15.9Hz), 6.56(2H, s), 6.75 (1H, s), 7.21–7.32(5H, m) 1.15(6H, d, J=7.0Hz), 2.30 (6H, s), 2.81(1H, m), 3.73 (3H, s), 4.44(2H, d, J=5.5 Hz), 5.78(1H, d, J=15.8 Hz),6.52(2H, s), 6.72–6.86(2H, m), 9.34(1H, s) | 187–188 |
| 67 | PhC≡CCH₂— | (CH₃)₂CH— | CH₃ | CH₃ | O | 1.15(6H, d, J=7.0Hz), 2.26 (6H, s), 2.79(1H, m), 4.75 (2H, s), 6.44(2H, s), 6.76 (1H, s), 7.21–7.33(5H, m), 8.82 (1H, s) | 186–187 |

EXAMPLE 68

Synthesis of 1-(cis-2-butenyl)-5-ethyl-6-(3,5-dimethylbenzoyl)-2,4-pyrimidinedione To a solution of 49 mg (0.15 mmol) of the compound obtained from Example 49 in 1 ml of methanol were added 3 ml of pyridine, a drop of quinoline, and 3 mg of palladium on barium sulfate. The reaction mixture was then stirred for about 2 hours at room temperature under an atmosphere of hydrogen, filtered through Cellite pad, and evaporated under reduced pressure to give a light brown oil, which was purified by flash chromatography using a mixture of ethyl acetate and hexane (1:2) as an eluent to afford 22 mg (yield 45%) of the title compound as a white solid.

M.p.: 199° to 200° C. ¹H-NMR(200 MHz, CDCl₃) δ 0.96(3H, t, J=7.3 Hz), 1.43(3H, dd, J=7.0 Hz, 1.8 Hz), 2.02(1H, m), 2.30(1H, m), 2.40(6H, s), 4.09(1H, m), 4.43 (1H, m), 5.23–5.54(2H, m), 7.34(1H, s), 7.52(2H, s), 8.45 (1H, s)

EXAMPLE 69

Synthesis of 1-(cis-cinnamyl)-5-ethyl-6-(3,5-dimethylbenzoyl)-2,4-pyrimidinedione To a solution of 40 mg (0.1 mmol) of the compound obtained from Example 50 in 1 ml of methanol were added 3 ml of pyridine, a drop of quinoline, and 4 mg of palladium on barium sulfate. The reaction mixture was then stirred for about 2 hours at room temperature under an atmosphere of hydrogen, filtered through Cellite pad, and evaporated under reduced pressure to give a light brown oil, which was purified by flash chromatography using a mixture of ethyl acetate and hexane (1:3) as an eluent to afford 28 mg (yield 69%) of the title compound as a white solid.

M.p.: 98° to 99° C. ¹H-NMR(200 MHz, CDCl₃) δ 0.95 (3H, t, J=7.3 Hz), 1.99(1H, m), 2.17–2.39(7H, m), 4.35(1H, m), 4.65(1H, m), 5.56(1H, m), 6.43(1H, d, J=11.6 Hz), 6.90–6.94(2H, m), 7.12–7.27(6H, m), 9.40(1H, s)

EXAMPLE 70

Synthesis of 1-(cis-2-butenyl)-5-ethyl-6-(3,5-dimethylphenoxy)-2,4-pyrimidinedione To a solution of 40 mg (0.13 mmol) of the compound obtained from Example 58 in 1 ml of methanol were added 3 ml of pyridine, a drop of quinoline, and 4 mg of palladium on barium sulfate. The reaction mixture was then stirred for about 2 hours at room temperature under an atmosphere of hydrogen, filtered through Cellite pad, and evaporated under reduced pressure to give a light brown oil, which was purified by flash chromatography using a mixture of ethyl acetate and hexane (1:3) as an eluent to afford 32 mg (yield 80%) of the title compound as a white solid.

M.p.: 181° to 182° C. ¹H-NMR(200 MHz, CDCl₃) δ 0.94(3H, t, J=7.5 Hz), 1.61(3H, dd, J=7.0 Hz, 1.5 Hz), 2.20(2H, q, J=7.5 Hz), 2.30(6H, s), 4.39(2H, d, J=7.0 Hz), 5.33–5.66(2H, m), 6.55(2H, s), 6.77(1H, s), 8.91(1H, s)

EXAMPLE 71

Synthesis of 1-(cis-2-butenyl)-5-isopropyl-6-(3,5-dimethylphenoxy)-2,4-pyrimidinedione To a solution of 33 mg (0.1 mmol) of the compound obtained from Example 11 in 1 ml of methanol were added 3 ml of pyridine, a drop of quinoline, and 4 mg of palladium on barium sulfate. The reaction mixture was then stirred for about 2 hours at room temperature under an atmosphere of hydrogen, filtered through Cellite pad, and evaporated under reduced pressure to give a light brown oil, which was purified by flash chromatography using a mixture of ethyl acetate and hexane (1:3) as an eluent to afford 25 mg (yield 76%) of the title compound as a white solid.

M.p.: 141° to 142° C. ¹H-NMR(200 MHz, CDCl₃) δ 1.13(6H, d, J=7.1 Hz), 1.61(3H, dd, J=6.9 Hz, 1.4 Hz), 2.31(6H, s), 2.79(1H, m), 4.35(2H, d, J=6.8 Hz), 5.38(1H, m), 5.60(1H, m), 6.54(2H, s), 6.77(1H, s)

EXAMPLE 72

Synthesis of 1-(ethoxycarbonylallyl)-5-ethyl-6-(3,5-dimethylbenzoyl)-2,4-pyrimidinedione To a solution of 100 mg (0.27 mmol) of the compound obtained from Example 8 in 10 ml of anhydrous ethanol was added 20 mg of p-toluenesulfonic acid monohydrate. The reaction mixture was refluxed with stirring for about 48 hours, neutralized with sodium bicarbonate, and evaporated under reduced pressure to give a light brown residue, which was purified by flash chromatography using a mixture of ethyl acetate and hexane (1:2) as an eluent to afford 60 mg (yield 58%) of the title compound as a white solid.

M.p.: 157° to 158° C. ¹H-NMR(200 MHz, CDCl₃) δ 0.98(3H, t, J=7.4 Hz), 1.22(3H, t, J=7.0 Hz), 2.07(1H, m), 2.27(1H, m), 2.39(6H, s), 4.08–4.37(4H, m), 5.66(1H, m), 6.66(1H, m), 7.33(1H, s), 7.51(2H, s), 9.24(1H, s)

EXAMPLE 73

Synthesis of 1-(isopropoxycarbonylallyl)-5-ethyl-6-(3,5-dimethylbenzoyl)-2,4-pyrimidinedione To a stirred solution of 100 mg (0.27 mmol) of the compound obtained from Example 8 in 10 ml of isopropyl alcohol was added 20 mg of p-toluenesulfonic acid monohydrate. The reaction mixture was refluxed with stirring for about 24 hours, neutralized with sodium bicarbonate, and evaporated under reduced pressure to give a light brown residue, which was purified by flash chromatography using a mixture of ethyl acetate and hexane (1:1) as an eluent to afford 40 mg (yield 37%) of the title compound as a white solid.

M.p.: 175° to 176° C. $^1$H-NMR(200 MHz, CDCl$_3$) δ 0.95(3H, t, J=7.4 Hz), 1.19(6H, d, J=6.0 Hz), 2.07(1H, m), 2.25(1H, m), 2.38(6H, s), 4.25–4.32(2H, m), 4.96(1H, m), 5.60(1H, m), 6.61(1H, m), 7.30(1H, s), 7.48(2H, s), 9.74 (1H, s)

EXAMPLE 74

Synthesis of 1-(4-azido-trans-2-butenyl)-5-isopropyl-6-(3,5-dimethylbenzoyl)-2,4-pyrimidinedione To a stirred solution of 187 mg (0.5 mmol) of the compound obtained from Example 9 in 5 ml of DMF was added 98 mg (1.5 mmol) of sodium azide at room temperature. After 24 hours, the reaction mixture was diluted with ether, washed with water, dried over anhydrous magnesium sulfate, and evaporated under reduced pressure to give a yellow oil, which was purified by flash chromatography using a mixture of ethyl acetate and hexane (1:2) as an eluent to afford 180 mg (yield 94%) of the title compound as a white solid.

M.p.: 126° to 127° C. $^1$H-NMR(200 MHz, CDCl$_3$) δ 1.14(3H, d, J=6.8 Hz), 1.21(3H, d, J=6.8 Hz), 2.31(1H, m), 2.39(6H, s), 3.60(2H, d, J=5.4 Hz), 4.03(1H, m), 4.31(1H, dd, J=15.8 Hz, 6.6 Hz), 5.40–5.70(2H, m), 7.34(1H, s), 7.53(2H, s), 9.91(1H, s)

EXAMPLE 75

Synthesis of 1-(4-acetoxy-trans-2-butenyl)-5-isopropyl-6-(3,5-dimethylbenzoyl)-2,4-pyrimidinedione To a solution of 187 mg (0.5 mmol) of the compound obtained from Example 9 in 5 ml of DMF was added 410 mg (5 mmol) of sodium acetate. The reaction mixture was then stirred for about 48 hours at 100° C., and evaporated under reduced pressure to give a yellow-colored residue, which was purified by flash chromatography using a mixture of ethyl acetate and hexane (1:2) as an eluent to afford 140 mg (yield 70%) of the title compound as a colorless syrup.

$^1$H-NMR(200 MHz, CDCl$_3$) δ 1.22(3H, d, J=6.9 Hz), 1.27(3H, d, J=6.8 Hz), 2.03(3H, s), 2.29(1H, m), 2.40(6H, s), 4.15(2H, m), 4.35(2H, d, J=4.7 Hz), 5.45–5.60(2H, m), 7.34(1H, s), 7.53(2H, s), 8.88(1H, s)

EXAMPLE 76

Synthesis of 1-(4-hydroxy-trans-2-butenyl)-5-isopropyl-6-(3,5-dimethylbenzoyl)-2,4-pyrimidinedione To a stirred solution of 80 mg (0.2 mmol) of the compound obtained from Example 75 in 5 ml of methanol was added 20 mg (0.37 mmol) of sodium methoxide at room temperature. After 1 hour, the reaction mixture was neutralized with acetic acid and evaporated under reduced pressure to give a yellow-colored residue, which was purified by flash chromatography using a mixture of ethyl acetate and hexane (4:1) as an eluent to afford 60 mg (yield 82%) of the title compound as a colorless syrup.

$^1$H-NMR(200 MHz, CDCl$_3$) δ 1.12(3H, d, J=6.8 Hz), 1.19(3H, d, J=6.8 Hz), 2.26–2.38(7H, m), 3.94–4.05(3H, m), 4.26(1H, dd, J=14.9 Hz, 4.4 Hz), 5.53–5.60(2H, m), 7.33 (1H, s), 7.52(2H, s), 9.56(1H, s)

EXAMPLE 77

Synthesis of 1-(carboxyallyl)-5-ethyl-6-(3,5-dimethylphenylthio)-2,4-pyrimidinedione To a stirred solution of 561 mg (1.5 mmol) of the compound obtained from Example 21 in 11 ml of methanol-water (10:1) was added 120 mg (3 mmol) of sodium hydroxide. The reaction mixture was then refluxed for about 2 hours, acidified with dil. hydrochloric acid, and evaporated under reduced pressure to give a yellow residue, which was purified by flash chromatography using a mixture of methanol and chloroform (1:9) as an eluent to afford 100 mg (yield 19%) of the title compound as a foam.

$^1$H-NMR(200 MHz, CDCl$_3$) δ 1.08(3H, t, J=7.5 Hz), 2.28(6H, s), 2.75(2H, q, J=7.5 Hz), 4.75–4.77(2H, m), 5.62(1H, d, J=15.8 Hz), 6.73–6.87(4H,m), 10.02(1H, s)

EXAMPLE 78

Synthesis of 1-(4-hydroxy-trans-2-butenyl)-5-ethyl-6-(3,5-dimethylphenylthio)-2,4-pyrimidinedione With stirring, a solution of 112 mg (0.3 mmol) of the compound obtained from Example 21 in 3 ml of THF was cooled to −78° C. under nitrogen and then 440 μl (0.66 mmol) of 1.5M solution of diisobutyl aluminum hydride in toluene was added. The resulting mixture was then warmed to room temperature over about 1 hour and stirred for 2 hours at room temperature. The excess hydride was then decomposed by addition of methanol and the solvent was removed under reduced pressure to give an oily residue, which was purified by flash chromatography using a mixture of methanol and chloroform (1:10) as an eluent to afford 47 mg (yield 45%) of the title compound as a white solid.

M.p.: 157° to 158° C. $^1$H-NMR(200 MHz, CDCl$_3$) δ 1.05(3H, t, J=7.4 Hz), 2.28(6H, s), 2.71(2H, q, J=7.4 Hz), 4.03–4.09(2H, m), 4.59–4.62(2H, m), 5.62–5.70(2H, m), 6.76(2H, s), 6.88(1H, s), 9.17(1H, s)

EXAMPLE 79

Synthesis of 1-(4-azido-trans-2-butenyl)-5-ethyl-6-(3,5-dimethylbenzoyl)-2,4-pyrimidinedione To a stirred solution of 200 mg (0.55 mmol) of the compound obtained from Example 47 in 5 ml of DMF was added 108 mg (1.66 mmol) of sodium azide at room temperature. After 18 hours, the reaction mixture was diluted with ether, washed with water, dried over anhydrous magnesium sulfate, and evaporated under reduced pressure to give a yellow-colored residue, which was purified by flash chromatography using a mixture of ethyl acetate and hexane (1:2) as an eluent to afford 184 mg (yield 90%) of the title compound as a white solid.

M.p.: 119° to 120° C. $^1$H-NMR(200 MHz, CDCl$_3$) δ 0.96(3H, t, J=7.4 Hz), 2.04(1H, m), 2.29(1H, m), 2.40(6H, s), 3.63(2H, d, J=5.5 Hz), 4.06(1H, m), 4.36(1H, m), 5.41–5.68(2H, m), 7.35(1H, s), 7.52(2H, s), 9.44(1H, s)

EXAMPLE 80

Synthesis of 1-(4-acetoxy-trans-2-butenyl)-5-ethyl-6-(3,5-dimethylbenzoyl)-2,4-pyrimidinedione To a solution of 180 mg (0.5 mmol) of the compound obtained from Example 47 in 5 ml of DMF was added 410 mg (5 mmol) of sodium acetate. The reaction mixture was then stirred for about 40 hours at 100° C. and evaporated under reduced pressure to give a yellow residue, which was purified by flash chromatography using a mixture of ethyl acetate and hexane (1:2) as an eluent to afford 110 mg (yield 57%) of the title compound as a white solid.

M.p.: 152° to 153° C. $^1$H-NMR(200 MHz, CDCl$_3$) δ 0.94(3H, t, J=7.4 Hz), 1.94–2.15(4H, m), 2.23(1H,m), 2.37 (6H, s), 4.00–4.35(4H, m), 5.44–5.65(2H, m), 7.32(1H, s), 7.49(2H, s), 9.67(1H,s)

EXAMPLE 81

Synthesis of 1-(4-hydroxy-trans-2-butenyl)-5-ethyl-6-(3,5-dimethylbenzoyl)-2,4-pyrimidinedione To a stirred solution of 50 mg (0.13 mmol) of the compound obtained from Example 80 in 5 ml of methanol was added 20 mg (0.37 mmol) of sodium methoxide at room temperature. After 1 hour, the reaction mixture was neutralized with acetic acid and evaporated under reduced pressure to give a yellow-colored residue, which was purified by flash chromatography using a mixture of ethyl acetate and hexane (4:1) as an eluent to afford 26 mg (yield 56%) of the title compound as a white solid.

M.p.: 172° to 173° C. $^1$H-NMR(200 MHz, CDCl$_3$) δ 0.96(3H, t, J=7.4 Hz), 2.01(1H, m), 2.31(1H, m), 2.40(6H, s), 3.94–4.37(4H, m), 5.57–5.62(2H, m), 7.34(1H, s), 7.52 (2H, s), 9.46(1H,s)

EXAMPLE 82

Synthesis of 1-(4-methoxy-trans-2-butenyl)-5-ethyl-6-(3,5-dimethylbenzoyl)-2,4-pyrimidinedione To a stirred solution of 60 mg (0.17 mmol) of the compound obtained from Example 47 in 2 ml of methanol was added 50 mg (2.17 mmol) of sodium under nitrogen at room temperature. After 48 hours, the reaction mixture was neutralized with acetic acid and evaporated under reduced pressure to give a yellow-colored residue, which was purified by flash chromatography using a mixture of ethyl acetate and hexane (1:1) as an eluent to afford 30 mg (yield 50%) of the title compound as a white solid.

M.p.: 142° to 143° C. $^1$H-NMR(200 MHz, CDCl$_3$) δ 0.95(3H, t, J=7.5 Hz), 2.01(1H, m), 2.27(1H, m), 2.39(6H, s), 3.24(3H, s), 3.73(2H, d, J=4.4 Hz), 4.07(1H, m), 4.32 (1H, m), 5.45–5.64(2H, m), 7.33(1H, s), 7.51(2H, s)

EXAMPLE 83

Synthesis of 1-(4-hydroxy-trans-2-butenyl)-5-ethyl-6-(3,5-dimethylphenoxy)-2,4-pyrimidinedione With stirring, a solution of 179 mg (0.53 mmol) of the compound obtained from Example 63 in 5 ml of THF was cooled to −78° C. under nitrogen and 1 ml (1.5 mmol) of 1.5M solution of diisobutyl aluminum hydride in toluene was added. The reaction mixture was then warmed to room temperature over about 2 hours, then stirred for 14 hours at room temperature. The excess hydride was then decomposed by addition of methanol and the solvent was removed under reduced pressure to give an oily residue, which was purified by flash chromatography using ether as an eluent to afford 66 mg (yield 40%) of the title compound as a white solid.

M.p.: 125° to 126° C. $^1$H-NMR(200 MHz, CDCl$_3$) δ 0.94(3H, t, J=7.4 Hz), 2.15–2.30(8H, m), 4.04–4.06(2H, m), 4.33–4.35(2H, m), 5.67–5.72(2H, m), 6.54(2H, s), 6.77(1H, s), 9.06(1H,s)

Antiviral Activity and Toxicity Test

The anti-HIV assays were based on the inhibition of the virus-induced cytopathic effect in MT-4 cells as described in J. Virol. Methods, 16, 171 (1987). Briefly, MT-4 cells were suspended in culture medium at 2.5×10$^5$ cells/ml and infected with 1000 CCID$_{50}$ (50% cell culture infective dose) of HIV. Immediately, after virus infection, 100 μl of the cell suspension was brought into each well of a flat-bottomed microtiter tray containing various concentrations of the test compounds. After a 4 or 5 day incubation at 37° C., the number of viable cells was determined by the 3-(4,5-dimethylthiazol-2-yl)-2,5-diphenyltetrazolium bromide (MTT) method, as disclosed in J. Virol. Methods, 20, 309 (1988).

The cytotoxicity of the compounds of the present invention was assessed in parallel with their antiviral activity. It was based on the viability of mock-infected host cells as determined by the MTT methods (se J. Virol. Methods, 20, 309 (1988)).

The results of the tests are shown in Table 2.

TABLE 2

| Ex. No. | CD$_{50}$ (μg/ml) | ED$_{50}$ (μg/ml) | S.I. (CD$_{50}$/ED$_{50}$) |
|---|---|---|---|
| 1 | 14.85 | <0.32 | >46 |
| 2 | 8.73 | <0.32 | >29 |
| 3 | 7.94 | <0.009 | >882 |
| 4 | 52.5 | <0.32 | >164 |
| 5 | 48.59 | <0.032 | >1,518 |
| 6 | 8.03 | <0.009 | >892 |
| 7 | 27.84 | <0.33 | >84 |
| 8 | 27.24 | <0.19 | >143 |
| 9 | 6.38 | <0.009 | >708 |
| 10 | 19.39 | <0.01 | >1,939 |
| 11 | 39.87 | <0.32 | >124 |
| 12 | 17.48 | <0.32 | >54 |
| 13 | 16.17 | <0.32 | >50 |
| 14 | 5.77 | <0.032 | >180 |
| 15 | 11.26 | 0.36 | 31 |
| 16 | 19.03 | 2.78 | 6.85 |
| 17 | 5.79 | 3.68 | 1.57 |
| 18 | 3.9 | <0.032 | >121 |
| 19 | 8.74 | <0.0.09 | >971 |
| 20 | 5.21 | <0.009 | >578 |
| 21 | 41.42 | <0.32 | >129 |
| 22 | 33.8 | <0.36 | >93 |
| 23 | 38.2 | <0.93 | >41 |
| 24 | 1.81 | <0.032 | >56 |
| 25 | 62.5 | <0.69 | >90 |
| 26 | 4.93 | <0.009 | >547 |
| 27 | 6.66 | <0.009 | >740 |
| 28 | 5.79 | <0.009 | >643 |
| 29 | 37.15 | <0.023 | >1,615 |
| 30 | 17.7 | <0.009 | >1,966 |
| 31 | 16.94 | <0.32 | >52 |
| 32 | 32.36 | <0.32 | >101 |
| 33 | 8.58 | <0.032 | >268 |
| 34 | 12.33 | <0.32 | >38 |
| 35 | 5.78 | <0.009 | 642 |
| 36 | 22.07 | <0.33 | 66 |
| 37 | 12.47 | 1.64 | 7.6 |
| 38 | 24.15 | <0.32 | >75 |
| 39 | 8.65 | <0.049 | >176 |
| 40 | 5.02 | <0.009 | >557 |
| 41 | 21.04 | 0.01 | >2,104 |
| 42 | 7.42 | <0.009 | >824 |
| 43 | 54.51 | <0.17 | >320 |
| 44 | 34.39 | <0.01 | >3,439 |
| 45 | 5.97 | <0.009 | >663 |
| 46 | 9.14 | <0.009 | >1,015 |
| 47 | 6.7 | <0.009 | >774 |
| 48 | 36.38 | <0.39 | >93 |
| 49 | 5.2 | <0.032 | >162 |
| 50 | 4.34 | <0.009 | >482 |

TABLE 2-continued

| Ex. No. | CD$_{50}$ (μg/ml) | ED$_{50}$ (μg/ml) | S.I. (CD$_{50}$/ED$_{50}$) |
|---|---|---|---|
| 51 | 22.26 | <0.01 | >2,473 |
| 52 | 9.75 | <0.009 | >1,083 |
| 53 | 5.99 | <0.009 | >665 |
| 54 | 30.05 | <0.01 | >3,005 |
| 55 | 41.66 | <0.32 | >130 |
| 56 | 6.76 | <0.009 | >75.1 |
| 57 | 42.39 | <0.32 | >132 |
| 58 | 48.9 | <0.34 | >143 |
| 59 | 38.56 | <0.23 | >167 |
| 60 | 15.76 | <0.62 | >25 |
| 61 | 9.3 | <0.009 | >1,033 |
| 62 | 8.05 | <0.032 | >251 |
| 63 | 7.17 | <0.032 | >224 |
| 64 | 9.89 | <0.009 | >1,098 |
| 65 | 8.04 | <0.009 | >893 |
| 66 | 78.64 | <0.32 | >245 |
| 67 | 7.6 | <0.009 | >844 |
| 68 | 8.21 | <0.032 | >162 |
| 69 | 8.67 | <0.032 | >270 |
| 70 | 73.81 | <0.01 | >7,381 |
| 71 | 7.71 | <0.0155 | >497 |
| 72 | 6.85 | <0.01 | >685 |
| 73 | 4.85 | <0.01 | >485 |
| 74 | 8.59 | <0.009 | >954 |
| 75 | 58.39 | <0.009 | >6,487 |
| 76 | 41.98 | <0.025 | >1,679 |
| 77 | 68.34 | <0.902 | >75 |
| 78 | 28.97 | <0.97 | >29 |
| 79 | 8.2 | <0.009 | >911 |
| 80 | 44.4 | <0.033 | >1,345 |
| 84 | 55.44 | <0.009 | >6,160 |
| 82 | 43.1 | <0.32 | >134 |
| 83 | 25.5 | <0.81 | >31 |
| Ref. 1 | 44.66 | <0.009 | >4,962 |
| Ref. 2 | 6.05 | <0.009 | >672 |

Footnote:
ED$_{50}$: Effective concentration for the inhibition of the proliferation of HIV by 50%
CD$_{50}$: Cytotoxic concentration that causes death of cells by 50%
S.I.: Selectivity index (CD$_{50}$/ED$_{50}$)
Ref. 1: 1-ethoxymethyl-5-ethyl-6-(3,5-dimethylbenzyl)-2,4-pyrimidinedione
Ref. 2: 1-benzyloxymethyl-5-ethyl-6-(3,5-dimethylphenylthio)-2,4-pyrimidinedione While the invention has been described in connection with the above specific embodiments, it should be recognized that various modifications and changes may be made to the present invention and also fall within the scope of the invention as defined by the claims that follow.

What is claimed is:

1. A 2,4-pyrimidinedione compound of formula(I):

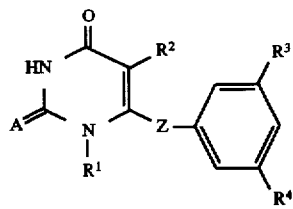

wherein:

R$^1$ represents an allyl, propargyl, substituted allyl group represented by CH$_2$CH=CR$^5$R$^6$ or substituted propargyl group represented by CH$_2$C≡CR$^7$, wherein R$^5$, R$^6$ and R$^7$ are each independently a hydrogen atom; a methyl group optionally substituted with a halogen atom, C$_{1-10}$ carbonyloxy, hydroxy, azido, cyano, amino, phenyl, C$_{1-3}$ alkoxy or benzyloxy radical; C$_{2-10}$ alkyl; cyclopropyl; phenyl; or C$_{2-10}$ ester group;

R$^2$ represents a halogen atom, a C$_{1-15}$ alkyl, C$_{3-6}$ cycloalkyl, C$_{2-8}$ alkenyl, C$_{2-8}$ alkynyl or benzyl group;

R$^3$ and R$^4$ represent independently a hydrogen or halogen atom, or a hydroxy, C$_{1-3}$ alkyl, fluoromethyl, C$_{1-3}$ alkoxy, amino, C$_{2-6}$ alkylester or C$_{2-7}$ alkylamide group;

A represents an oxygen or sulfur atom; and

Z represents an oxygen or sulfur atom; a carbonyl group; an amino group; or a methylene group optionally substituted with one or more selected from the group consisting of a halogen atom, and a cyano, a hydroxy, an azido, an amino, a C$_{1-3}$ alkylamide, a C$_{1-4}$ ester, and a nitro groups, or a pharmaceutically acceptable salt thereof.

2. The compound of claim 1 wherein A is an oxygen atom and Z is an oxygen or sulfur atom, or a carbonyl or methylene group, or a pharmaceutically acceptable salt thereof.

3. The compound of claim 2 wherein R$^2$ is an ethyl or isopropyl group, R$^3$ and R$^4$ are independently a hydrogen or halogen atom, or a hydroxy, C$_{1-3}$ alkyl, fluoromethyl or C$_{1-3}$ alkoxy group, or a pharmaceutically acceptable salt thereof.

4. A pharmaceutical composition comprising an antivirally effective amount of the 2,4-pyrimidinedione compound or a pharmaceutically acceptable salt thereof defined in claim 1 as an active ingredient, and pharmaceutically acceptable carrier and/or adjuvants.

5. A compound having the formula (II):

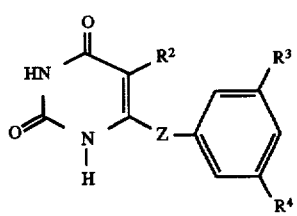

wherein:

R$^2$ is an ethyl or isopropyl group.

R$^3$ and R$^4$ are each a hydrogen or halogen atom, or a hydroxy, C$_{1-3}$ alkyl, fluoromethyl or C$_{1-3}$ alkoxy group.

Z is an oxygen or sulfur atom, or a carbonyl or methylene group.

* * * * *

UNITED STATES PATENT AND TRADEMARK OFFICE

CERTIFICATE OF CORRECTION

PATENT NO.    : 5,747,500
DATED         : May 5, 1998
INVENTOR(S)   : Jong-Chan Son, et al It is certified that error appears in the above-identified patent and that said Letters Patent is hereby corrected as shown below:

On the title page, item:

[75]  Inventors: JONG-CHAN SON; ILL-YOUNG LEE, both of Daejeon; BYUNG-IL BAE, Seoul; JEONG-SIK HAN; JOONG-KWON CHOI, both of Daejeon; YUNG-BOK CHAE, Seoul, all of Rep of Korea Signed and Sealed this Third Day of November, 1998

Attest:

BRUCE LEHMAN

*Attesting Officer*

*Commissioner of Patents and Trademarks*